United States Patent
Tonks et al.

(10) Patent No.: US 6,552,169 B1
(45) Date of Patent: Apr. 22, 2003

(54) DENSITY ENHANCED PROTEIN TYROSINE PHOSPHATASES

(75) Inventors: Nicholas K. Tonks, Huntington, NY (US); Arne Ostman, Uppsala (SE)

(73) Assignee: Cold Spring Harbor Laboratory, Cold Spring Harbor, NY (US)

( * ) Notice: Subject to any disclaimer, the term of this patent is extended or adjusted under 35 U.S.C. 154(b) by 0 days.

(21) Appl. No.: 09/447,533

(22) Filed: Nov. 23, 1999

Related U.S. Application Data

(63) Continuation of application No. 08/854,585, filed on May 12, 1997, now Pat. No. 6,114,140, which is a continuation of application No. 08/237,940, filed on May 3, 1994, now abandoned.

(51) Int. Cl.$^7$ .......................... C07K 14/47; C12N 5/10; C12N 9/00; C12N 15/52; C12N 15/63
(52) U.S. Cl. ...................... 530/350; 536/23.2; 435/69.1; 435/325; 435/320.1; 435/71.1; 435/71.2; 435/471; 435/252.3; 435/254.11; 435/196
(58) Field of Search .................. 530/350; 536/23.1, 536/23.2; 435/69.1, 325, 320.1, 71.1, 71.2, 471, 252.3, 254.11, 196

(56) References Cited

U.S. PATENT DOCUMENTS

| | | |
|---|---|---|
| 5,441,880 A | 8/1995 | Beach et al. |
| 5,512,434 A | 4/1996 | Aaronson et al. |

FOREIGN PATENT DOCUMENTS

| | | |
|---|---|---|
| WO | WO 94/03610 | 2/1994 |

OTHER PUBLICATIONS

Mikayama et al. Proc. Natl. Acad. Sci. USA. vol. 90, pp. 10056–10060, 1993.*
Voet et al. Biochemistry. John Wiley & Sons, Inc. pp. 126–128 & 228–234, 1990.*
Barnea et al., "Idnetification of a Carbonic Anyhydrase–Like Domain in the Extracellular Region of RPTPγ Defines a New Subfamily of Receptor Tyrosine Phosphatases," *Mol. Cell. Biol.* 13:1497–1506, 1993.
Bork and Doolittle, "Proposed Acquisition of an Animal Protein Domain by Bacteria," *Proc. Natl. Acad. Sci. USA* 89:8990–8994, 1992.
Brady–Kalnay et al., "Homophilic Binding of a PTPμ, a Receptor–Type Protein Phospharase, Can Mediate Cell–Cell Aggregation," *J. Cell Biol.* 122:961–972, 1993.
Brown–Shimer et al., "Effect of Protein Tyrosine Phosphatase 1B Expression on Transformation by the Human neu Oncogene," *Cancer Res.* 52:478–482, 1992.
Buzzi et al., "Differentiation–Induced Changes in Protein–Tyrosine Phosphatase . . . ," *Cancer Res.* 52:4027–4035, 1992.
Capecchi, "Altering the Genome by Homologous Recombination," *Science* 244:1288–1292, 1989.
Carr et al., "Association of the Type II cAMP–dependent Protein Kinase with a Human Thyroid RII–Anchoring Protein," *J. Biol. Chem.* 267:13376–13382, 1992.
Carr and Scott, "Blotting and Bandshifting: Techniques for Studying Protein–Protein Interactions," *Trends in Biochemical Sci.* 17:246–249, 1992.
Charbonneau and Tonks, "1002 Protein Phosphatases," *Ann. Rev. Cell Biol.* 8:463–493, 1993.
Cool et al., "cDNA Isolated from a Human T–Cell Library Encodes a Member of the Protein–Tyrosine–Phosphatase Family," *Proc. Natl. Acad. Sci. USA* 86:5257–5261, 1989.
Edelman and Crossin, "Cell Adhesion Molecules: Implications for a Molecular Histology," *Ann Rev. Biochem.* 60:155–190, 1991.
Fields and Song, "A Novel Genetic System to Detech Protein–Protein Interactions," *Nature* 340:245–246, 1989.
Fischer et al., "Protein Tyrosine Phosphatases: A Diverse Family of Intracellular and Transmembrane Enzymes," *Science* 253:401–406, 1991.
Flint et al., "Multi–site Phosphorylation of the Protein Tyrosine Phosphatase, PTPIB: Identification of Cell Cycle Regulated and Phorbol Ester Stimulated Sites of Phosphorylation," *EMBO J.* 12:1937–1946, 1993.
Frangioni et al., "The Nontransmembrani Tyrosine Phosphatase PTP–B1 Lacalizes to the Endoplasmic Reticulum Via its 35 Amino Acid C–Terminal Sequence," *Cell* 68:545–560, 1992.
Gebbink et al., "Cloning, Expression and Chromosomal Localization of a New Putative Receptor–Like Protein Tyrosine Phosphatase," *FEBS Lett.* 290:123–130, 1991.
Gu et al., "Cloning and Expression of a Cytosolic Megakarycyte Protein–Tyrosine–Phosphatase with a Sequence Homology to Retinaldchyde–Binding Protein and Yeast SEC14p," *Proc. Natl. Acad. Sci. USA* 89:2980–2984, 1992.
Hirsch et al., "Cloning and Expression of an Intron–less Gene for AKAP 75, an Anchor Protein for the Regulatory Subunit of cAMP–Dependent Protein Kinase IIβ," *J. Biol. Chem.* 267:2131–2134, 1992.
Honda et al., "Identification of Novel Protein–Tyrosine Phosphatases . . . ," *Leukemia* 7(5):742–746, 1993.
Honda et al., "Molecular Cloning Characterization and Chromosomal Localization of a Novel Protein–Tyrosine Phosphatase HPTP$_1$," *Blood* 84(12):4186–4194, 1994.
Huynh et al., "Constructing and Screening cDNA Libraries in Agt10 and Agt11," *DNA Cloning,* edited by Glover, IRL Press, pp. 49–78, 1985.

(List continued on next page.)

Primary Examiner—Prema Mertz
(74) Attorney, Agent, or Firm—Seed Intellectual Property Law Group PLLC

(57) ABSTRACT

Novel Type III density enhanced protein tyrosine phosphatases are disclosed and exemplified by human DEP-1 enzyme. Polynucleotides encoding huDEP-1 are disclosed, along with methods and materials for production of the same by recombinant procedures. Binding molecules specific for DEP-1 are also disclosed as useful for modulating the biological activities of DEP-1.

2 Claims, 2 Drawing Sheets

OTHER PUBLICATIONS

Klarlund, "Transformation of Cells by an Inhibitor of Phosphatases Acting on Phosphotyrosine in Proteins," *Cell* 41:707–717, 1985.

Kozak, "The Scanning Model for Translation: An Update," *J. Cell Biol.* 108:229–241, 1989.

Krueger et al., "Structural Diversity and Evolution of Human Receptor–like Protein Tyrosine Phosphatases," *EMBO J.* 9:3241–3252, 1990.

Krueger and Saito, "A Human Transmembrane Protein–Tyrosine–Phosphatase, PTPξ, is Expressed in Brain and has an N–terminal Receptor Domain Homologous to Carbonic Anhydrase," *Proc. Notl. Acad. Sci. USA* 89:74717–7421, 1992.

Leahy et al., "Structure of a Fibronectin Type III Domain from Tenascin Phased by MAD Analysis of the Selenomethionyl Protein," *Science* 258:987–991, 1992.

Longo et al., "Leukocyte Common Antigen–Related Receptor–linked Tyrosine Phosphatase," *J. Biol. Chem.* 268:26503–25611, 1993.

Main et al., "The Three Dimensional Structure of the Tenth Type III Module of Fibronectin an Insight into RGD–mediated Interactions," *Cell* 71:671–678, 1992.

Matozaki et al., "Molecular Cloning of a Human Transmembrane–type Protein Tyrosine Phosphatase and its Expression in Gastrointestinal Cancers," *J. Biol. Chem.* 269:2075–2081, 1994.

Oon et al., "Alternative Splicing in a Novel Tyrosine Phosphatase Gene (DPTP4E) of *Drosophila Melanogaster* Generates Two Large Receptor–Like Proteins which Differ in their Corboxyl Termini," *J. Biol. Chem.* 268:23964–23971, 1993.

Pallen and Tong, "Elevation of Membrane Tyrosine Phosphatase Activity in Density–Dependent Growth–Arrested Fibroblasts," *Proc. Natl. Acad. Sci. USA* 88:6996–7000, 1991.

Patthy, "Homology of a Domain of the Growth Hormone/Prolactin Receptor Family with Type III Modules of Fibronectin," *Cell* 61:13–14, 1992.

Pingel and Thomas, "Evidence that the Leukocyte Common Antigen is Required for Anitgen–Induced T Lymphocyte Proliferation," *Cell* 58:1055–1065, 1989.

Rijksen et al., "Orthovanadate Both Mimics and Antagonizes the Transforming Growth Factor β Action on Normal Rat Kidney Cells," *J. Cell Physiol.* 154:393–401, 1993.

Sambrook et al., *Molecular Cloning,* CSH Laboratory Press, 1989, pp. 16.17–16.22.

Sambrook et al., *Molecular Cloning,* CSH Laboratory Press, 1989, pp. 16.32–16.40.

Schultz et al., "Mutations at the Murine Motheaten Locus are within the Hematopoietic Cell Protein–Tyrosine Phosphatase (Hcph) Gene," *Cell* 73:1445–1454, 1993.

Schwarzbauer, "Fibronectin: From Gene to Protein," *Curr. Opin. Cell. Biol.* 3:786–791, 1991.

Scott and Smith, "Searching for Peptide Ligands with an Epitope Library," *Science* 249:386–390, 1990.

Seed and Aruffo, "Molecular Cloning of the CD2 Antigen, the T–Cell Erythrocyte Receptor, by a Rapid Immunoselection Procedure," *Proc. Natl. Acad. Sci. USA* 84:3365–3369, 1987.

Stoker and Rubin, "Density Dependent Inhibition of Cell Growth in Culture," *Nature* 215:171–172, 1967.

Streuli et al., "A New Member of the Immunoglobulin Superfamily that has a Cytoplasmic Region Homologous to the Leukocyte Common Antigen," *J. Exp. Med.* 168:1523–1530, 1988.

Streuli et al., "Expression of the Receptor–like Protein Tyrosine Phosphatase LAR: Proteolytic Cleavage and Shedding of CAM–Like Extracellular Region," *EMBO J.* 11:897–907, 1992.

Sun et al., "MKP–1 (3CH134), an Immediate Early Gene Product, is a Dual Specificity Phophatase that Dephosphorylates MAP Kinase In Vivo," *Cell* 75:487–493, 1993.

Tian et al., "Three Receptor–Linked Protein–Tyrosine Phosphatases are Selectively Expressed on Central Nervous System Axons in the Drosophila Embryo," *Cell* 67:675–685, 1991.

Tonks et al., "Purification of the Major Protein–Tyrosine Phosphatases of Human Placenta," *J. Biol. Chem.* 263:6722–6730, 1988.

Tonks, "Protein Phosphatases: Key Players in the Regulation of Cell Function," *Curr. Opin. Cell. Biol.* 2:1114–1124, 1990.

Vojtek et al., "Mammalian RAS Interacts directly with the Serine Threonine Kinase Raf," *Cell* 74:205–214, 1993.

Wary et al., "A Homozygous Deletion Within the Carbonic Anhydrase–Like Domain of the Ptprg Gene in Murine L–Cells," *Cancer Res.* 53:1498–1502, 1993.

Yang and Tonks, "Isolation of cDNA Clone Encoding a Human Protein–Tyrosine Phosphatase with Homology to the Cytoskeletal–Associated Proteins Band 4.1, Erzin, Talin," *Proc. Natl. Acad. Sci. USA* 88:5949–5953, 1991.

Yang et al., "A Protein Kinase Substrate Identified by the Two–Hybrid System," *Science* 257:680–682, 1992.

Yang et al., "Two Drosophila Receptor–like Tyrosine Phosphatase Genes are Expressed in a Subset of Developing Axons and Pioneer Neurons in the Embryonic CNS," *Cell* 67:661–673, 1991.

Young and Davis, "Efficient Isolation of Genes by Using Antibody Probes," *Proc. Natl. Acad. Sci. USA* 80:1194–1198, 1983.

* cited by examiner

SEQUENCE LISTING (1) GENERAL INFORMATION:

(iii) NUMBER OF SEQUENCES: 6

(2) INFORMATION FOR SEQ ID NO: 1:

(i) SEQUENCE CHARACTERISTICS:
        (A) LENGTH: 5117 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 350..4361

(xi) SEQUENCE DESCRIPTION: SEQ ID NO: 1:

```
CCCCAGCCGC ATGACGCGCG GAGGAGGCAG CGGGACGAGC GCGGGAGCCG GGACCGGGTA      60

GCCGCGCGCT GGGGGTGGGC GCCGCTCGCT CCGCCCCGCG AAGCCCCTGC GCGCTCAGGG     120

ACGCGGCCCC CCCGCGGCAG CCGCGCTAGG CTCCGGCGTG TGGCCGCGGC CGCCGCCGCG     180

CTGCCATGTC TCCGGGGAAG CCGGGGCGGG CGGAGCGGGG ACGAGGCGGA CCGGCTGGCG     240

GAGGAGGAGG CGAAGGAGAC GGCAGGAGGC GGCGACGACG GTGCCCGGGC TCGGGCGCAC     300

GGCGGGGCCC GATTCGCGCG TCCGGGGCAC GTTCCAGGGC GCGCGGGGC ATG AAG         355
                                                      Met Lys
                                                        1

CCG GCG GCG CGG GAG GCG CGG CTG CCT CCG CGC TCG CCC GGG CTG CGC       403
Pro Ala Ala Arg Glu Ala Arg Leu Pro Pro Arg Ser Pro Gly Leu Arg
        5                  10                  15

TGG GCG CTG CCG CTG CTG CTG CTG CTG CTG CGC CTG GGC CAG ATC CTG       451
Trp Ala Leu Pro Leu Leu Leu Leu Leu Leu Arg Leu Gly Gln Ile Leu
    20                  25                  30

TGC GCA GGT GGC ACC CCT AGT CCA ATT CCT GAC CCT TCA GTA GCA ACT       499
Cys Ala Gly Gly Thr Pro Ser Pro Ile Pro Asp Pro Ser Val Ala Thr
35                  40                  45                  50

GTT GCC ACA GGG GAA AAT GGC ATA ACG CAG ATC AGC AGT ACA GCA GAA       547
Val Ala Thr Gly Glu Asn Gly Ile Thr Gln Ile Ser Ser Thr Ala Glu
                55                  60                  65

TCC TTT CAT AAA CAG AAT GGA ACT GGA ACA CCT CAG GTG GAA ACA AAC       595
Ser Phe His Lys Gln Asn Gly Thr Gly Thr Pro Gln Val Glu Thr Asn
            70                  75                  80

ACC AGT GAG GAT GGT GAA AGC TCT GGA GCC AAC GAT AGT TTA AGA ACA       643
Thr Ser Glu Asp Gly Glu Ser Ser Gly Ala Asn Asp Ser Leu Arg Thr
        85                  90                  95
```

```
CCT GAA CAA GGA TCT AAT GGG ACT GAT GGG GCA TCT CAA AAA ACT CCC       691
Pro Glu Gln Gly Ser Asn Gly Thr Asp Gly Ala Ser Gln Lys Thr Pro
    100                 105                 110

AGT AGC ACT GGG CCC AGT CCT GTG TTT GAC ATT AAA GCT GTT TCC ATC       739
Ser Ser Thr Gly Pro Ser Pro Val Phe Asp Ile Lys Ala Val Ser Ile
115                 120                 125                 130

AGT CCA ACC AAT GTG ATC TTA ACT TGG AAA AGT AAT GAC ACA GCT GCT       787
Ser Pro Thr Asn Val Ile Leu Thr Trp Lys Ser Asn Asp Thr Ala Ala
                135                 140                 145

TCT GAG TAC AAG TAT GTA GTA AAG CAT AAG ATG GAA AAT GAG AAG ACA       835
Ser Glu Tyr Lys Tyr Val Val Lys His Lys Met Glu Asn Glu Lys Thr
            150                 155                 160

ATT ACT GTT GTG CAT CAA CCA TGG TGT AAC ATC ACA GGC TTA CGT CCA       883
Ile Thr Val Val His Gln Pro Trp Cys Asn Ile Thr Gly Leu Arg Pro
        165                 170                 175

GCG ACT TCA TAT GTA TTC TCC ATC ACT CCA GGA ATA GGC AAT GAG ACT       931
Ala Thr Ser Tyr Val Phe Ser Ile Thr Pro Gly Ile Gly Asn Glu Thr
    180                 185                 190

TGG GGA GAT CCC AGA GTC ATA AAA GTC ATC ACA GAG CCG ATC CCA GTT       979
Trp Gly Asp Pro Arg Val Ile Lys Val Ile Thr Glu Pro Ile Pro Val
195                 200                 205                 210

TCT GAT CTC CGT GTT GCT CAC GGG TGT GAG GAA GGC TGC TCT CTC TCC      1027
Ser Asp Leu Arg Val Ala His Gly Cys Glu Glu Gly Cys Ser Leu Ser
                215                 220                 225

TGG AGC AAT GGC AAT GGC ACC GCC TCC TGC CGG GTT CTT CTT GAA AGC      1075
Trp Ser Asn Gly Asn Gly Thr Ala Ser Cys Arg Val Leu Leu Glu Ser
            230                 235                 240

ATT GGA AGC CAT GAG GAG TTG ACT CAA GAC TCA AGA CTT CAG GTC AAT      1123
Ile Gly Ser His Glu Glu Leu Thr Gln Asp Ser Arg Leu Gln Val Asn
        245                 250                 255

ATC TCG GAC CTG AAG CCA GGG GTT CAA TAC AAC ATC AAC CCG TAT CTT      1171
Ile Ser Asp Leu Lys Pro Gly Val Gln Tyr Asn Ile Asn Pro Tyr Leu
    260                 265                 270

CTA CAA TCA AAT AAG ACA AAG GGA GAC CCC TTG GCA CAG AAG GTG GCT      1219
Leu Gln Ser Asn Lys Thr Lys Gly Asp Pro Leu Ala Gln Lys Val Ala
275                 280                 285                 290

TGG ATG CCA GCA ATA CAG AGA GAA GCC GGG CAG GGA GCC CCA CCG CCC      1267
Trp Met Pro Ala Ile Gln Arg Glu Ala Gly Gln Gly Ala Pro Pro Pro
                295                 300                 305

CTG TGC ATG ATG AGT CCC TTC GTG GGA CCT GTG GAC CCA TCC TCC GGC      1315
Leu Cys Met Met Ser Pro Phe Val Gly Pro Val Asp Pro Ser Ser Gly
            310                 315                 320

CAG CAG TCC CGA GAC ACG GAA GTC CTG CTT GTC GGG TTA GAG CCT GGC      1363
Gln Gln Ser Arg Asp Thr Glu Val Leu Leu Val Gly Leu Glu Pro Gly
        325                 330                 335

ACC CGA TAC AAT GCC ACC GTT TAT TCC CAA GCA GCG AAT GGC ACA GAA      1411
Thr Arg Tyr Asn Ala Thr Val Tyr Ser Gln Ala Ala Asn Gly Thr Glu
    340                 345                 350

GGA CAG CCC CAG GCC ATA GAG TTC AGG ACA AAT GCT ATT CAG GTT TTT      1459
Gly Gln Pro Gln Ala Ile Glu Phe Arg Thr Asn Ala Ile Gln Val Phe
355                 360                 365                 370

GAC GTC ACC GCT GTG AAC ATC AGT GCC ACA AGC CTG ACC CTG ATC TGG      1507
Asp Val Thr Ala Val Asn Ile Ser Ala Thr Ser Leu Thr Leu Ile Trp
                375                 380                 385

AAA GTC AGC GAT AAC GAG TCG TCA TCT AAC TAT ACC TAC AAG ATA CAT      1555
Lys Val Ser Asp Asn Glu Ser Ser Ser Asn Tyr Thr Tyr Lys Ile His
            390                 395                 400

GTG GCG GGG GAG ACA GAT TCT TCC AAT CTC AAC GTC AGT GAG CCT CGC      1603
Val Ala Gly Glu Thr Asp Ser Ser Asn Leu Asn Val Ser Glu Pro Arg
```

```
                    405                 410                 415
GCT GTC ATC CCC GGA CTC CGC TCC AGC ACC TTC TAC AAC ATC ACA GTG    1651
Ala Val Ile Pro Gly Leu Arg Ser Ser Thr Phe Tyr Asn Ile Thr Val
        420                 425                 430

TGT CCT GTC CTA GGT GAC ATC GAG GGC ACG CCG GGC TTC CTC CAA GTG    1699
Cys Pro Val Leu Gly Asp Ile Glu Gly Thr Pro Gly Phe Leu Gln Val
435                 440                 445                 450

CAC ACC CCC CCT GTT CCA GTT TCT GAC TTC CGA GTG ACA GTG GTC AGC    1747
His Thr Pro Pro Val Pro Val Ser Asp Phe Arg Val Thr Val Val Ser
                455                 460                 465

ACG ACG GAG ATC GGC TTA GCA TGG AGC AGC CAT GAT GCA GAA TCA TTT    1795
Thr Thr Glu Ile Gly Leu Ala Trp Ser Ser His Asp Ala Glu Ser Phe
            470                 475                 480

CAG ATG CAT ATC ACA CAG GAG GGA GCT GGC AAT TCT CGG GTA GAA ATA    1843
Gln Met His Ile Thr Gln Glu Gly Ala Gly Asn Ser Arg Val Glu Ile
        485                 490                 495

ACC ACC AAC CAA AGT ATT ATC ATT GGT GGC TTG TTC CCT GGA ACC AAG    1891
Thr Thr Asn Gln Ser Ile Ile Ile Gly Gly Leu Phe Pro Gly Thr Lys
    500                 505                 510

TAT TGC TTT GAA ATA GTT CCA AAA GGA CCA AAT GGG ACT GAA GGG GCA    1939
Tyr Cys Phe Glu Ile Val Pro Lys Gly Pro Asn Gly Thr Glu Gly Ala
515                 520                 525                 530

TCT CGG ACA GTT TGC AAT AGA ACT GTT CCC AGT GCA GTG TTT GAC ATC    1987
Ser Arg Thr Val Cys Asn Arg Thr Val Pro Ser Ala Val Phe Asp Ile
                535                 540                 545

CAC GTG GTC TAC GTC ACC ACC ACG GAG ATG TGG CTG GAC TGG AAG AGC    2035
His Val Val Tyr Val Thr Thr Thr Glu Met Trp Leu Asp Trp Lys Ser
            550                 555                 560

CCT GAC GGT GCT TCC GAG TAT GTC TAC CAT TTA GTC ATA GAG TCC AAG    2083
Pro Asp Gly Ala Ser Glu Tyr Val Tyr His Leu Val Ile Glu Ser Lys
        565                 570                 575

CAT GGC TCT AAC CAC ACA AGC ACG TAT GAC AAA GCG ATT ACT CTC CAG    2131
His Gly Ser Asn His Thr Ser Thr Tyr Asp Lys Ala Ile Thr Leu Gln
    580                 585                 590

GGC CTG ATT CCG GGC ACC TTA TAT AAC ATC ACC ATC TCT CCA GAA GTG    2179
Gly Leu Ile Pro Gly Thr Leu Tyr Asn Ile Thr Ile Ser Pro Glu Val
595                 600                 605                 610

GAC CAC GTC TGG GGG GAC CCC AAC TCC ACT GCA CAG TAC ACA CGG CCC    2227
Asp His Val Trp Gly Asp Pro Asn Ser Thr Ala Gln Tyr Thr Arg Pro
                615                 620                 625

AGC AAT GTG TCC AAC ATT GAT GTA AGT ACC AAC ACC ACA GCA GCA ACT    2275
Ser Asn Val Ser Asn Ile Asp Val Ser Thr Asn Thr Thr Ala Ala Thr
            630                 635                 640

TTA AGT TGG CAG AAC TTT GAT GAC GCC TCT CCC ACG TAC TCC TAC TGC    2323
Leu Ser Trp Gln Asn Phe Asp Asp Ala Ser Pro Thr Tyr Ser Tyr Cys
        645                 650                 655

CTT CTT ATT GAG AAG GCT GGA AAT TCC AGC AAC GCA ACA CAA GTA GTC    2371
Leu Leu Ile Glu Lys Ala Gly Asn Ser Ser Asn Ala Thr Gln Val Val
    660                 665                 670

ACG GAC ATT GGA ATT ACT GAC GCT ACA GTC ACT GAA TTA ATA CCT GGC    2419
Thr Asp Ile Gly Ile Thr Asp Ala Thr Val Thr Glu Leu Ile Pro Gly
675                 680                 685                 690

TCA TCA TAC ACA GTG GAG CTC TTT GCA CAA GTA GGG GAT GGG ATC AAG    2467
Ser Ser Tyr Thr Val Glu Leu Phe Ala Gln Val Gly Asp Gly Ile Lys
                695                 700                 705

TCA CTG GAA CCT GGC CGG AAG TCA TTC TGT ACA GAT CCT GCG TCC ATG    2515
Ser Leu Glu Pro Gly Arg Lys Ser Phe Cys Thr Asp Pro Ala Ser Met
            710                 715                 720

GCC TCC TTC GAC TGC GAA GTG GTC CCC AAA GAG CCA GCC CTG GTT CTC    2563
```

```
                                                          -continued

Ala Ser Phe Asp Cys Glu Val Val Pro Lys Glu Pro Ala Leu Val Leu
    725                 730                 735

AAA TGG ACC TGC CCT CCT GGC GCC AAT GCA GGC TTT GAG CTG GAG GTC    2611
Lys Trp Thr Cys Pro Pro Gly Ala Asn Ala Gly Phe Glu Leu Glu Val
740                 745                 750

AGC AGT GGA GCC TGG AAC AAT GCG ACC CAC CTG GAG AGC TGC TCC TCT    2659
Ser Ser Gly Ala Trp Asn Asn Ala Thr His Leu Glu Ser Cys Ser Ser
755                 760                 765                 770

GAG AAT GGC ACT GAG TAT AGA ACG GAA GTC ACG TAT TTG AAT TTT TCT    2707
Glu Asn Gly Thr Glu Tyr Arg Thr Glu Val Thr Tyr Leu Asn Phe Ser
            775                 780                 785

ACC TCG TAC AAC ATC AGC ATC ACC ACT GTG TCC TGT GGA AAG ATG GCA    2755
Thr Ser Tyr Asn Ile Ser Ile Thr Thr Val Ser Cys Gly Lys Met Ala
                790                 795                 800

GCC CCC ACC CGG AAC ACC TGC ACT ACT GGC ATC ACA GAT CCC CCT CCT    2803
Ala Pro Thr Arg Asn Thr Cys Thr Thr Gly Ile Thr Asp Pro Pro Pro
            805                 810                 815

CCA GAT GGA TCC CCT AAT ATT ACA TCT GTC AGT CAC AAT TCA GTA AAG    2851
Pro Asp Gly Ser Pro Asn Ile Thr Ser Val Ser His Asn Ser Val Lys
820                 825                 830

GTC AAG TTC AGT GGA TTT GAA GCC AGC CAC GGA CCC ATC AAA GCC TAT    2899
Val Lys Phe Ser Gly Phe Glu Ala Ser His Gly Pro Ile Lys Ala Tyr
835                 840                 845                 850

GCT GTC ATT CTC ACC ACC GGG GAA GCT GGT CAC CCT TCT GCA GAT GTC    2947
Ala Val Ile Leu Thr Thr Gly Glu Ala Gly His Pro Ser Ala Asp Val
            855                 860                 865

CTG AAA TAC ACG TAT GAC GAT TTC AAA AAG GGA GCC TCA GAT ACT TAT    2995
Leu Lys Tyr Thr Tyr Asp Asp Phe Lys Lys Gly Ala Ser Asp Thr Tyr
        870                 875                 880

GTG ACA TAC CTC ATA AGA ACA GAA GAA AAG GGA CGT TCT CAG AGC TTG    3043
Val Thr Tyr Leu Ile Arg Thr Glu Glu Lys Gly Arg Ser Gln Ser Leu
            885                 890                 895

TCT GAA GTT TTG AAA TAT GAA ATT GAC GTT GGG AAT GAG TCA ACC ACA    3091
Ser Glu Val Leu Lys Tyr Glu Ile Asp Val Gly Asn Glu Ser Thr Thr
900                 905                 910

CTT GGT TAT TAC AAT GGG AAG CTG GAA CCT CTG GGC TCC TAC CGG GCT    3139
Leu Gly Tyr Tyr Asn Gly Lys Leu Glu Pro Leu Gly Ser Tyr Arg Ala
915                 920                 925                 930

TGT GTG GCT GGC TTC ACC AAC ATT ACC TTC CAC CCT CAA AAC AAG GGG    3187
Cys Val Ala Gly Phe Thr Asn Ile Thr Phe His Pro Gln Asn Lys Gly
            935                 940                 945

CTC ATT GAT GGG GCT GAG AGC TAT GTG TCC TTC AGT CGC TAC TCA GAT    3235
Leu Ile Asp Gly Ala Glu Ser Tyr Val Ser Phe Ser Arg Tyr Ser Asp
            950                 955                 960

GCT GTT TCC TTG CCC CAG GAT CCA GGT GTC ATC TGT GGA GCG GTT TTT    3283
Ala Val Ser Leu Pro Gln Asp Pro Gly Val Ile Cys Gly Ala Val Phe
            965                 970                 975

GGC TGT ATC TTT GGT GCC CTG GTT ATT GTG ACT GTG GGA GGC TTC ATC    3331
Gly Cys Ile Phe Gly Ala Leu Val Ile Val Thr Val Gly Gly Phe Ile
980                 985                 990

TTC TGG AGA AAG AAG AGG AAA GAT GCA AAG AAT AAT GAA GTG TCC TTT    3379
Phe Trp Arg Lys Lys Arg Lys Asp Ala Lys Asn Asn Glu Val Ser Phe
995                 1000                1005                1010

TCT CAA ATT AAA CCT AAA AAA TCT AAG TTA ATC AGA GTG GAG AAT TTT    3427
Ser Gln Ile Lys Pro Lys Lys Ser Lys Leu Ile Arg Val Glu Asn Phe
                1015                1020                1025

GAG GCC TAC TTC AAG AAG CAG CAA GCT GAC TCC AAC TGT GGG TTC GCA    3475
Glu Ala Tyr Phe Lys Lys Gln Gln Ala Asp Ser Asn Cys Gly Phe Ala
            1030                1035                1040
```

```
GAG GAA TAC GAA GAT CTG AAG CTT GTT GGA ATT AGT CAA CCT AAA TAT      3523
Glu Glu Tyr Glu Asp Leu Lys Leu Val Gly Ile Ser Gln Pro Lys Tyr
        1045                1050                1055

GCA GCA GAA CTG GCT GAG AAT AGA GGA AAG AAT CGC TAT AAT AAT GTT      3571
Ala Ala Glu Leu Ala Glu Asn Arg Gly Lys Asn Arg Tyr Asn Asn Val
1060                1065                1070

CTG CCC TAT GAT ATT TCC CGT GTC AAA CTT TCG GTC CAG ACC CAT TCA      3619
Leu Pro Tyr Asp Ile Ser Arg Val Lys Leu Ser Val Gln Thr His Ser
1075                1080                1085                1090

ACG GAT GAC TAC ATC AAT GCC AAC TAC ATG CCT GGC TAC CAC TCC AAG      3667
Thr Asp Asp Tyr Ile Asn Ala Asn Tyr Met Pro Gly Tyr His Ser Lys
                1095                1100                1105

AAA GAT TTT ATT GCC ACA CAA GGA CCT TTA CCG AAC ACT TTG AAA GAT      3715
Lys Asp Phe Ile Ala Thr Gln Gly Pro Leu Pro Asn Thr Leu Lys Asp
        1110                1115                1120

TTT TGG CGT ATG GTT TGG GAG AAA AAT GTA TAT GCC ATC ATT ATG TTG      3763
Phe Trp Arg Met Val Trp Glu Lys Asn Val Tyr Ala Ile Ile Met Leu
                1125                1130                1135

ACT AAA TGT GTT GAA CAG GGA AGA ACC AAA TGT GAG GAG TAT TGG CCC      3811
Thr Lys Cys Val Glu Gln Gly Arg Thr Lys Cys Glu Glu Tyr Trp Pro
        1140                1145                1150

TCC AAG CAG GCT CAG GAC TAT GGA GAC ATA ACT GTG GCA ATG ACA TCA      3859
Ser Lys Gln Ala Gln Asp Tyr Gly Asp Ile Thr Val Ala Met Thr Ser
1155                1160                1165                1170

GAA ATT GTT CTT CCG GAA TGG ACC ATC AGA GAT TTC ACA GTG AAA AAT      3907
Glu Ile Val Leu Pro Glu Trp Thr Ile Arg Asp Phe Thr Val Lys Asn
                1175                1180                1185

ATC CAG ACA AGT GAG AGT CAC CCT CTG AGA CAG TTC CAT TTC ACC TCC      3955
Ile Gln Thr Ser Glu Ser His Pro Leu Arg Gln Phe His Phe Thr Ser
        1190                1195                1200

TGG CCA GAC CAC GGT GTT CCC GAC ACC ACT GAC CTG CTC ATC AAC TTC      4003
Trp Pro Asp His Gly Val Pro Asp Thr Thr Asp Leu Leu Ile Asn Phe
                1205                1210                1215

CGG TAC CTC GTT CGT GAC TAC ATG AAG CAG AGT CCT CCC GAA TCG CCG      4051
Arg Tyr Leu Val Arg Asp Tyr Met Lys Gln Ser Pro Pro Glu Ser Pro
        1220                1225                1230

ATT CTG GTG CAT TGC AGT GCT GGG GTC GGA AGG ACG GGC ACT TTC ATT      4099
Ile Leu Val His Cys Ser Ala Gly Val Gly Arg Thr Gly Thr Phe Ile
1235                1240                1245                1250

GCC ATT GAT CGT CTC ATC TAC CAG ATA GAG AAT GAG AAC ACC GTG GAT      4147
Ala Ile Asp Arg Leu Ile Tyr Gln Ile Glu Asn Glu Asn Thr Val Asp
                1255                1260                1265

GTG TAT GGG ATT GTG TAT GAC CTT CGA ATG CAT AGG CCT TTA ATG GTG      4195
Val Tyr Gly Ile Val Tyr Asp Leu Arg Met His Arg Pro Leu Met Val
        1270                1275                1280

CAG ACA GAG GAC CAG TAT GTT TTC CTC AAT CAG TGT GTT TTG GAT ATT      4243
Gln Thr Glu Asp Gln Tyr Val Phe Leu Asn Gln Cys Val Leu Asp Ile
        1285                1290                1295

GTC AGA TCC CAG AAA GAC TCA AAA GTA GAT CTT ATC TAC CAG AAC ACA      4291
Val Arg Ser Gln Lys Asp Ser Lys Val Asp Leu Ile Tyr Gln Asn Thr
        1300                1305                1310

ACT GCA ATG ACA ATC TAT GAA AAC CTT GCG CCC GTG ACC ACA TTT GGA      4339
Thr Ala Met Thr Ile Tyr Glu Asn Leu Ala Pro Val Thr Thr Phe Gly
1315                1320                1325                1330

AAG ACC AAT GGT TAC ATC GCC TAAT TCCAAAGGAA TAACCTTTCT               4384
Lys Thr Asn Gly Tyr Ile Ala
                1335

GGAGTGAACC AGACCGTCGC ACCCACAGCG AAGGCACATG CCCCGATGTC GACATGTTTT    4444

TATATGTCTA ATATCTTAAT TCTTTGTTCT GTTTTGTGAG AACTAATTTT GAGGGCATGA    4504
```

```
AGCTGCATAT GATAGATGAC AAATTGGGGC TGTCGGGGGC TGTGGATGGG TGGGGAGCAA    4564

ATCATCTGCA TTCCTGATGA CCAATGGGAT GAGGTCACTT TTTTTTTTTT CCCCCTTGAG    4624

GATTGCGGAA AACCAGGAAA AGGGATCTAT GATTTTTTTT TCCAAAACAA TTTCTTTTTT    4684

AAAAAGACTA TTTTATATGA TTCACATGCT AAAGCCAGGA TTGTGTTGGG TTGAATATAT    4744

TTTAAGTATC AGAGGTCTAT TTTTACCTAC TGTGTCTTGG AATCTAGCCG ATGGAAAATA    4804

CCTAATTGTG GATGATGATT GCGCAGGGAG GGGTACGTGG CACCTCTTCC GAATGGGTTT    4864

TCTATTTGAA CATGTGCCTT TTCTGAATTA TGCTTCCACA GGCAAAACTC AGTAGAGATC    4924

TATATTTTTG TACTGAATCT CATAATTGGA ATATACGGAA TATTTAAACA GTAGCTTAGC    4984

ATCAGAGGTT TGCTTCCTCA GTAACATTTC TGTTCTCATT TGATCAGGGG AGGCCTCTTT    5044

GCCCCGGCCC CGCTTCCCCT GCCCCCGTGT GATTTGTGCT CCATTTTTTC TTCCCTTTTC    5104

CCTCCCAGTT TTC                                                      5117
```

(2) INFORMATION FOR SEQ ID NO: 2:

(i) SEQUENCE CHARACTERISTICS:
        (A) LENGTH: 1337 amino acids
        (B) TYPE: amino acid
        (D) TOPOLOGY: linear (ii) MOLECULE TYPE: protein (xi) SEQUENCE DESCRIPTION: SEQ ID NO: 2:

```
Met Lys Pro Ala Ala Arg Glu Ala Arg Leu Pro Pro Arg Ser Pro Gly
  1               5                  10                  15

Leu Arg Trp Ala Leu Pro Leu Leu Leu Leu Leu Arg Leu Gly Gln
             20                  25                  30

Ile Leu Cys Ala Gly Gly Thr Pro Ser Pro Ile Pro Asp Pro Ser Val
             35                  40                  45

Ala Thr Val Ala Thr Gly Glu Asn Gly Ile Thr Gln Ile Ser Ser Thr
 50                  55                  60

Ala Glu Ser Phe His Lys Gln Asn Gly Thr Gly Thr Pro Gln Val Glu
 65                  70                  75                  80

Thr Asn Thr Ser Glu Asp Gly Glu Ser Ser Gly Ala Asn Asp Ser Leu
             85                  90                  95

Arg Thr Pro Glu Gln Gly Ser Asn Gly Thr Asp Gly Ala Ser Gln Lys
            100                 105                 110

Thr Pro Ser Ser Thr Gly Pro Ser Pro Val Phe Asp Ile Lys Ala Val
            115                 120                 125

Ser Ile Ser Pro Thr Asn Val Ile Leu Thr Trp Lys Ser Asn Asp Thr
            130                 135                 140

Ala Ala Ser Glu Tyr Lys Tyr Val Val Lys His Lys Met Glu Asn Glu
145                 150                 155                 160

Lys Thr Ile Thr Val Val His Gln Pro Trp Cys Asn Ile Thr Gly Leu
            165                 170                 175

Arg Pro Ala Thr Ser Tyr Val Phe Ser Ile Thr Pro Gly Ile Gly Asn
            180                 185                 190

Glu Thr Trp Gly Asp Pro Arg Val Ile Lys Val Ile Thr Glu Pro Ile
            195                 200                 205

Pro Val Ser Asp Leu Arg Val Ala His Gly Cys Glu Glu Gly Cys Ser
            210                 215                 220

Leu Ser Trp Ser Asn Gly Asn Gly Thr Ala Ser Cys Arg Val Leu Leu
225                 230                 235                 240
```

-continued

```
Glu Ser Ile Gly Ser His Glu Glu Leu Thr Gln Asp Ser Arg Leu Gln
                245                 250                 255
Val Asn Ile Ser Asp Leu Lys Pro Gly Val Gln Tyr Asn Ile Asn Pro
            260                 265                 270
Tyr Leu Leu Gln Ser Asn Lys Thr Lys Gly Asp Pro Leu Ala Gln Lys
        275                 280                 285
Val Ala Trp Met Pro Ala Ile Gln Arg Glu Ala Gly Gln Gly Ala Pro
    290                 295                 300
Pro Pro Leu Cys Met Met Ser Pro Phe Val Gly Pro Val Asp Pro Ser
305                 310                 315                 320
Ser Gly Gln Gln Ser Arg Asp Thr Glu Val Leu Leu Val Gly Leu Glu
                325                 330                 335
Pro Gly Thr Arg Tyr Asn Ala Thr Val Tyr Ser Gln Ala Ala Asn Gly
            340                 345                 350
Thr Glu Gly Gln Pro Gln Ala Ile Glu Phe Arg Thr Asn Ala Ile Gln
        355                 360                 365
Val Phe Asp Val Thr Ala Val Asn Ile Ser Ala Thr Ser Leu Thr Leu
    370                 375                 380
Ile Trp Lys Val Ser Asp Asn Glu Ser Ser Ser Asn Tyr Thr Tyr Lys
385                 390                 395                 400
Ile His Val Ala Gly Glu Thr Asp Ser Ser Asn Leu Asn Val Ser Glu
                405                 410                 415
Pro Arg Ala Val Ile Pro Gly Leu Arg Ser Ser Thr Phe Tyr Asn Ile
            420                 425                 430
Thr Val Cys Pro Val Leu Gly Asp Ile Glu Gly Thr Pro Gly Phe Leu
        435                 440                 445
Gln Val His Thr Pro Pro Val Pro Val Ser Asp Phe Arg Val Thr Val
    450                 455                 460
Val Ser Thr Thr Glu Ile Gly Leu Ala Trp Ser Ser His Asp Ala Glu
465                 470                 475                 480
Ser Phe Gln Met His Ile Thr Gln Glu Gly Ala Gly Asn Ser Arg Val
                485                 490                 495
Glu Ile Thr Thr Asn Gln Ser Ile Ile Ile Gly Gly Leu Phe Pro Gly
            500                 505                 510
Thr Lys Tyr Cys Phe Glu Ile Val Pro Lys Gly Pro Asn Gly Thr Glu
        515                 520                 525
Gly Ala Ser Arg Thr Val Cys Asn Arg Thr Val Pro Ser Ala Val Phe
    530                 535                 540
Asp Ile His Val Val Tyr Val Thr Thr Thr Glu Met Trp Leu Asp Trp
545                 550                 555                 560
Lys Ser Pro Asp Gly Ala Ser Glu Tyr Val Tyr His Leu Val Ile Glu
                565                 570                 575
Ser Lys His Gly Ser Asn His Thr Ser Thr Tyr Asp Lys Ala Ile Thr
            580                 585                 590
Leu Gln Gly Leu Ile Pro Gly Thr Leu Tyr Asn Ile Thr Ile Ser Pro
        595                 600                 605
Glu Val Asp His Val Trp Gly Asp Pro Asn Ser Thr Ala Gln Tyr Thr
    610                 615                 620
Arg Pro Ser Asn Val Ser Asn Ile Asp Val Ser Thr Asn Thr Thr Ala
625                 630                 635                 640
Ala Thr Leu Ser Trp Gln Asn Phe Asp Asp Ala Ser Pro Thr Tyr Ser
                645                 650                 655
```

-continued

Tyr Cys Leu Leu Ile Glu Lys Ala Gly Asn Ser Ser Asn Ala Thr Gln
            660                 665                 670

Val Val Thr Asp Ile Gly Ile Thr Asp Ala Thr Val Thr Glu Leu Ile
            675                 680                 685

Pro Gly Ser Ser Tyr Thr Val Glu Leu Phe Ala Gln Val Gly Asp Gly
            690                 695                 700

Ile Lys Ser Leu Glu Pro Gly Arg Lys Ser Phe Cys Thr Asp Pro Ala
705                 710                 715                 720

Ser Met Ala Ser Phe Asp Cys Glu Val Val Pro Lys Glu Pro Ala Leu
            725                 730                 735

Val Leu Lys Trp Thr Cys Pro Pro Gly Ala Asn Ala Gly Phe Glu Leu
            740                 745                 750

Glu Val Ser Ser Gly Ala Trp Asn Asn Ala Thr His Leu Glu Ser Cys
            755                 760                 765

Ser Ser Glu Asn Gly Thr Glu Tyr Arg Thr Glu Val Thr Tyr Leu Asn
            770                 775                 780

Phe Ser Thr Ser Tyr Asn Ile Ser Ile Thr Thr Val Ser Cys Gly Lys
785                 790                 795                 800

Met Ala Ala Pro Thr Arg Asn Thr Cys Thr Thr Gly Ile Thr Asp Pro
            805                 810                 815

Pro Pro Pro Asp Gly Ser Pro Asn Ile Thr Ser Val Ser His Asn Ser
            820                 825                 830

Val Lys Val Lys Phe Ser Gly Phe Glu Ala Ser His Gly Pro Ile Lys
            835                 840                 845

Ala Tyr Ala Val Ile Leu Thr Thr Gly Glu Ala Gly His Pro Ser Ala
            850                 855                 860

Asp Val Leu Lys Tyr Thr Tyr Asp Phe Lys Lys Gly Ala Ser Asp
865                 870                 875                 880

Thr Tyr Val Thr Tyr Leu Ile Arg Thr Glu Glu Lys Gly Arg Ser Gln
            885                 890                 895

Ser Leu Ser Glu Val Leu Lys Tyr Glu Ile Asp Val Gly Asn Glu Ser
            900                 905                 910

Thr Thr Leu Gly Tyr Tyr Asn Gly Lys Leu Glu Pro Leu Gly Ser Tyr
            915                 920                 925

Arg Ala Cys Val Ala Gly Phe Thr Asn Ile Thr Phe His Pro Gln Asn
            930                 935                 940

Lys Gly Leu Ile Asp Gly Ala Glu Ser Tyr Val Ser Phe Ser Arg Tyr
945                 950                 955                 960

Ser Asp Ala Val Ser Leu Pro Gln Asp Pro Gly Val Ile Cys Gly Ala
            965                 970                 975

Val Phe Gly Cys Ile Phe Gly Ala Leu Val Ile Val Thr Val Gly Gly
            980                 985                 990

Phe Ile Phe Trp Arg Lys Lys Arg Lys Asp Ala Lys Asn Asn Glu Val
            995                 1000                1005

Ser Phe Ser Gln Ile Lys Pro Lys Lys Ser Lys Leu Ile Arg Val Glu
            1010                1015                1020

Asn Phe Glu Ala Tyr Phe Lys Lys Gln Gln Ala Asp Ser Asn Cys Gly
1025                1030                1035                1040

Phe Ala Glu Glu Tyr Glu Asp Leu Lys Leu Val Gly Ile Ser Gln Pro
            1045                1050                1055

Lys Tyr Ala Ala Glu Leu Ala Gly Asn Arg Gly Lys Asn Arg Tyr Asn
            1060                1065                1070

Asn Val Leu Pro Tyr Asp Ile Ser Arg Val Lys Leu Ser Val Gln Thr

```
                    1075                1080                    1085

His Ser Thr Asp Asp Tyr Ile Asn Ala Asn Tyr Met Pro Gly Tyr His
    1090                1095                    1100

Ser Lys Lys Asp Phe Ile Ala Thr Gln Gly Pro Leu Pro Asn Thr Leu
1105                1110                    1115                1120

Lys Asp Phe Trp Arg Met Val Trp Glu Lys Asn Val Tyr Ala Ile Ile
                1125                1130                    1135

Met Leu Thr Lys Cys Val Glu Gln Gly Arg Thr Lys Cys Glu Glu Tyr
                    1140                1145                1150

Trp Pro Ser Lys Gln Ala Gln Asp Tyr Gly Asp Ile Thr Val Ala Met
                1155                1160                1165

Thr Ser Glu Ile Val Leu Pro Glu Trp Thr Ile Arg Asp Phe Thr Val
    1170                1175                    1180

Lys Asn Ile Gln Thr Ser Glu Ser His Pro Leu Arg Gln Phe His Phe
1185                1190                1195                1200

Thr Ser Trp Pro Asp His Gly Val Pro Asp Thr Thr Asp Leu Leu Ile
                1205                1210                1215

Asn Phe Arg Tyr Leu Val Arg Asp Tyr Met Lys Gln Ser Pro Pro Glu
                1220                1225                1230

Ser Pro Ile Leu Val His Cys Ser Ala Gly Val Gly Arg Thr Gly Thr
                1235                1240                1245

Phe Ile Ala Ile Asp Arg Leu Ile Tyr Gln Ile Glu Asn Glu Asn Thr
    1250                1255                1260

Val Asp Val Tyr Gly Ile Val Tyr Asp Leu Arg Met His Arg Pro Leu
1265                1270                1275                1280

Met Val Gln Thr Glu Asp Gln Tyr Val Phe Leu Asn Gln Cys Val Leu
                1285                1290                1295

Asp Ile Val Arg Ser Gln Lys Asp Ser Lys Val Asp Leu Ile Tyr Gln
                1300                1305                1310

Asn Thr Thr Ala Met Thr Ile Tyr Glu Asn Leu Ala Pro Val Thr Thr
            1315                1320                1325

Phe Gly Lys Thr Asn Gly Tyr Ile Ala
    1330                1335

(2) INFORMATION FOR SEQ ID NO: 3:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 3:

Lys Cys Ala Gln Tyr Trp Pro
1               5

(2) INFORMATION FOR SEQ ID NO: 4:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 4:
```

```
His Cys Ser Ala Gly Ile Gly
1               5
```

(2) INFORMATION FOR SEQ ID NO: 5:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 5:

```
AARTGYGCNC ARTAYTGGCC                                              20
```

(2) INFORMATION FOR SEQ ID NO: 6:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 6
        (D) OTHER INFORMATION: /note= "N is inosine"

(xi) SEQUENCE DESCRIPTION: SEQ ID NO: 6:

```
CCDATNCCNG CRCTRCARTG                                              20
```

DENSITY ENHANCED PROTEIN TYROSINE PHOSPHATASES

CROSS REFERENCE TO RELATED APPLICATIONS

This application is a continuation of Ser. No. 08/854,585, filed May 12, 1997, now U.S. Pat. No. 6,114,140 which is a continuation of Ser. No. 08/237,240 filed May 3, 1994, now abandoned.

FIELD OF THE INVENTION

The present invention relates generally to purified and isolated protein tyrosine phosphatase enzymes (PTPs) and polynucleotides encoding the same. PTPs of the invention are characterized by upregulated mRNA transcription and/or translation, or post-translational modification leading to increased total cellular enzyme activity as a function of increased cellular contact with neighboring cells. Such density enhanced PTPs are referred to as DEPTPs. An illustrative human Type III receptor-like density-enhanced protein tyrosine phosphatase has been designated huDEP-1.

BACKGROUND OF THE INVENTION

Protein tyrosine phosphorylation is an essential element in signal transduction pathways which control fundamental cellular processes including growth and differentiation, cell cycle progression, and cytoskeletal function. Briefly, the binding of growth factors, or other ligands, to a cognate receptor protein tyrosine kinase (PTK) triggers autophosphorylation of tyrosine residues in the receptor itself and phosphorylation of tyrosine residues in the enzyme's target substrates. Within the cell, tyrosine phosphorylation is a reversible process; the phosphorylation state of a particular tyrosine residue in a target substrate is governed by the coordinated action of both (PTKs), catalyzing phosphorylation, and protein tyrosine phosphatases (PTPs), catalyzing dephosphorylation.

The PTPs are a large and diverse family of enzymes found ubiquitously in eukaryotes [Charbonneau and Tonks, Ann.Rev. Cell Biol. 8:463–493 (1993)]. Structural diversity within the PTP family arises primarily from variation in non-catalytic (potentially regulatory) sequences which are linked to one or more highly conserved catalytic domains. In general, soluble cytoplasmic PTP forms are termed non-receptor PTPs and those with at least one non-catalytic region that traverses the cell membrane are termed receptor-like PTPs (RPTPs).

A variety of non-receptor PTPs have been identified which characteristically possess a single catalytic domain flanked, by non-catalytic sequences. Such non-catalytic sequences have been shown to include, among others, sequences homologous to cytoskeletal-associated proteins [Yang and Tonks, Proc.Natl.Acad.Sci. (USA) 88:5949–5953 (1991)] or to lipid binding proteins [Gu, et al., Proc.Natl.Acad.Sci. (USA) 89:2980–2984 (1992)], and/or sequences that mediate association of the enzyme with specific intracellular membranes [Frangioni et al., Cell 68:545–560 (1992)], suggesting that subcellular localization may play a significant role in regulation of PTP activity.

Analysis of non-catalytic domain sequences of RPTPs suggests their involvement in signal transduction mechanisms. However, binding of specific ligands to the extracellular segment of RPTPs has been characterized in only a few instances. For example, homophilic binding has been demonstrated between molecules of PTPμ [Brady-Kalnay, et al., J. Cell. Biol. 122:961–972 (1993)] i.e., the ligand for PTPμ expressed on a cell surface is another PTPμ molecule on the surface of an adjacent cell. Little is otherwise known about ligands which specifically bind to, and modulate the activity of, the majority of RPTPs.

Many receptor-like PTPs comprise an intracellular carboxyl segment with two catalytic domains, a single transmembrane domain and an extracellular amino terminal segment [Krueger et al., EMBO J. 9:3241–3252 (1990)]. Subclasses of RPTPs are distinguished from one another on the basis of categories or "types" of extracellular domains [Fischer, et al., Science 253:401–406 (1991)]. Type I RPTPs have a large extracellular domain with multiple glycosylation sites and a conserved cysteine-rich region. CD45 is a typical Type I RPTP. The Type II RPTPs contain at least one amino terminal immunoglobulin (Ig)-like domain adjacent to multiple tandem fibronectin type III (FNIII)-like repeats. Similar repeated FNIII domains, believed to participate in protein:protein interactions, have been identified in receptors for IL2, IL4, IL6, GM-CSF, prolactin, erythropoietin and growth hormone [Patthy, Cell 61:13–14 (1992)]. The leukocyte common antigen-related PTP known as LAR exemplifies the Type II RPTP structure [Streuli et al., J.Exp.Med. 168:1523–1530 (1988)], and, like other Type II RPTPs, contains an extracellular region reminiscent of the NCAM class of cellular adhesion molecules [Edelman and Crossin, Ann.Rev.Biochem. 60:155–190 (1991)]. The Type III RPTPs, such as HPTPβ [Krueger et al., EMBO J. 9:3241–3252 (1990)], contain only multiple tandem FNIII repeats in the extracellular domain. The Type IV RPTPs, for example RPTPα [Krueger et al. (1990) supra], have relatively short extracellular sequences lacking cysteine residues but containing multiple glycosylation sites. A fifth type of RPTP, exemplified by PTPγ [Barnes, et al., Mol.Cell.Biol. 13:1497–1506 (1993)] and PTPζ [Krueger and Saito, Proc.Natl.Acad.Sci. (USA) 89:7417–7421 (1992)], is characterized by an extracellular domain containing a 280 amino acid segment which is homologous to carbonic anhydrase (CAH) but lacks essential histidine residues required for reversible hydration of carbon dioxide.

FNIII sequences characteristically found in the extracellular domains of Type II and Type III RPTPs comprise approximately ninety amino acid residues with a folding pattern similar to that observed for Ig-like domains [Bork and Doolittle, Proc.Natl.Acad.Sci(USA) 89:8990–8994 (1992)]. Highly conserved FNIII sequences have been identified in more than fifty different eukaryotic and prokaryotic proteins [Bork and Doolittle, Proc.Natl.Acad.Sci. (USA) 89:8990–8994 (1992)], but no generalized function has been established for these domains. Fibronectin itself contains fifteen to seventeen FNIII domain sequences, and it has been demonstrated that the second FNIII domain ($FNIII_2$) contains a binding site for heparin sulphate proteoglycan [Schwarzbauer, Curr.Opin.Cell Biol. 3:786–791 (1991)] and that $FNIII_{13}$ and $FNIII_{14}$ are responsible for heparin binding through ionic interactions [Schwarzbauer, Curr. Opin. Cell Biol. 3:786–791 (199 1)]. Perhaps the best characterized interaction for a fibronectin FNIII domain involves $FNIII_{10}$ which is the major site for cell adhesion [Edelman and Crossin, Ann.Rev.Biochem 60:155–190 (1991); Leahy, et al., Science 258:987–991 (1992); Main, et al., Cell 71:671–678 (1992)]. $FNIII_{10}$ contains the amino acid sequence Arg-Gly-Asp (RGD) which is involved in promoting cellular adhesion through binding to particular members of the integrin superfamily of proteins.

Characteristics shared by both the soluble PTPs and the RPTPs include an absolute specificity for phosphotyrosine residues, a high affinity for substrate proteins, and a specific activity which is one to three orders of magnitude in excess of that of the PTKs in vitro [Fischer, et al., *Science* 253:401–406 (1991); Tonks, *Curr.Opin.Cell.Biol.* 2:1114–1124 (1990)]. This latter characteristic suggests that PTP activity may exert an antagonistic influence on the action of PTKs in vivo, the balance between these two thus determining the level of intracellular tyrosine phosphorylation. Supporting a dominant physiological role for PTP activity is the observation that treatment of NRK-1 cells with vanadate, a potent inhibitor of PTP activity, resulted in enhanced levels of phosphotyrosine and generation of a transformed cellular morphology [Klarlund, *Cell* 41:707–717 (1985)]. This observation implies potential therapeutic value for PTPs and agents which modulate PTP activity as indirect modifiers of PTK activity, and thus, levels of cellular phosphotyrosine.

Recent studies have highlighted aspects of the physiological importance of PTP activity. For example, mutations in the gene encoding a non-receptor hematopoietic cell protein tyrosine phosphatase, HCP, have been shown to result in severe immune dysfunction characteristic of the motheaten phenotype in mice [Schultz, et al., *Cell* 73:1445–1454 (1993)]. Under normal conditions HCP may act as a suppressor of PTK-induced signaling pathways, for example, the CSF-1 receptor [Schultz, et al., *Cell* 73:1445–1454 (1993)]. Some PTP enzymes may be the products of tumor suppressor genes and their mutation or deletion may contribute to the elevation in cellular phosphotyrosine associated with certain neoplasias [Brown-Shimer, et al., *Cancer Res.* 52:478–482 (1992); Wary, et al., *Cancer Res.* 53:1498–1502 (1993)]. Mutations observed in the gene for RPTPγ in murine L cells would be consistent with this hypothesis [Wary, et al., *Cancer Res.* 53: 1498–1502 (1993)]. The observation that the receptor-like PTP CD45 is required for normal T cell receptor-induced signalling [Pingel and Thomas, *Cell* 58:1055–1065 (1989)] provides evidence implicating PTP activity as a positive mediator of cellular signalling responses.

Normal cells in culture exhibit contact inhibition of growth, i.e., as adjacent cells in a confluent monolayer touch each other, their growth is inhibited [Stoker and Rubin, *Nature* 215:171–172 (1967)]. Since PTKs promote cell growth, PTP action may underlie mechanisms of growth inhibition. In Swiss mouse 3T3 cells, a phosphatase activity associated with membrane fractions is enhanced eight-fold in confluent cells harvested at high density as compared to cells harvested from low or medium density cultures [Pallen and Tong, *Proc. Natl.Acad. Sci.* (*USA*) 88:6996–7000 (1991)]. This elevated activity was not observed in subconfluent cell cultures brought to quiescence by serum deprivation. The enhanced phosphatase activity was attributed to a 37 kD protein, as determined by gel filtration, but was not otherwise characterized. Similarly, PTPs have been directly linked to density arrest of cell growth; treatment of NRK-1 cells with vanadate was able to overcome density dependent growth inhibition and stimulate anchorage independent proliferation, a characteristic unique to transformed, or immortalized, cells [Klarland, *Cell* 41:707–717 (1985); Rijksen, et al., *J. Cell Physiol.* 154:343–401 (1993)].

In contrast to these observations, PCT Publication No. WO 94/03610 discloses a transmembrane PTP, termed PTP35, the steady state mRNA level of which was observed to be at a maximum in actively growing cells. Little or no PTP35 mRNA expression was detected in confluent cell. This mode of regulation was also observed in mouse 3T3 cells. Thus, two RPTPs in the same cell type apparently participate in opposing processes, with one (PTP35) contributing to cellular growth and the other (the 35 kD PTP of Pallen and Tongs) contributing to cellular quiescence.

Interestingly, transcription of Type II RPTP LAR messenger RNA has been demonstrated to be upregulated in confluent fibroblast cell culture [Longo, et al., *J.Biol.Chem.* 268:26503–26511 (1993)]. LAR is proteolytically processed to generate a mature protein that is a complex of two non-covalently associated subunits, one containing the majority of the cell adhesion molecule-like extracellular domain [Yu, et al., *Oncogene* 7:1051–1057 (1992); Streuli, et al., *EMBO J.* 11:897–907 (1992)] and which is shed as cells approach confluence [Streuli, et al., *EMBO J.* 11:897–907 (1992)]. These observations lead to speculation regarding PTP involvement in modulation of cytoskeletal integrity, as well as other related cellular phenomena such as transformation, tumor invasion, metastasis, cell adhesion, and leukocyte movement along and passage through the endothelial cell layer in inflammation. The therapeutic implications are enormous for modulators of PTP activity which are capable of regulating any or all of these cellular events.

There thus exists a need in the art to identify members of the PTP family of enzymes and to characterize these proteins in terms of their amino acid and encoding DNA sequences. Such information would provide for the large scale production of the proteins, allow for identification of cells which express the phosphatases naturally and permit production of antibodies specifically reactive with the phosphatases. Moreover, elucidation of the substrates, regulatory mechanisms, and subcellular localization of these PTPs would contribute to an understanding of normal cell growth and provide information essential for the development of therapeutic agents useful for intervention in abnormal and/or malignant cell growth.

BRIEF DESCRIPTION OF THE INVENTION

As employed herein with respect to a protein tyrosine phosphatase, "density enhanced" denotes upregulated cellular mRNA transcription or translation and/or total cellular activity as a function of increased contact with neighboring cells.

In one aspect, the present invention provides purified and isolated polynucleotides (e.g., DNA and RNA transcripts, both sense and anti-sense strands) encoding a Type III density enhanced protein tyrosine phosphatase enzymatic activity exemplified by the human phosphatase huDEP-1 and variants, including fragments, thereof (i.e., fragments and deletion, addition or substitution analogs) which possess binding and/or immunological properties inherent to Type III density enhanced phosphatases. Preferred DNA molecules of the invention include cDNA, genomic DNA and wholly or partially chemically synthesized DNA molecules. A presently preferred polynucleotide is the DNA as set forth in SEQ ID NO: 1, encoding the human DEP-1 polypeptide of SEQ ID NO: 2. Also provided are recombinant plasmid and viral DNA constructions (expression constructs) which include Type III density enhanced phosphatase encoding sequences, especially constructions wherein the Type III density enhanced phosphatase encoding sequence is operatively linked to a homologous or heterologous transcriptional regulatory element or elements.

As another aspect of the invention, prokaryotic or eukaryotic host cells transformed or transfected with DNA sequences of the invention are provided which express a Type III density enhanced phosphatase polypeptide or variants thereof. Host cells of the invention are particularly useful for large scale production of Type III density enhanced phosphatase polypeptides, which can be isolated from either the host cell itself or the medium in which the host cell is grown. Host cells which express Type III density enhanced phosphatase polypeptides on the extracellular membrane surface are also useful as immunogens in the production of anti-Type III density enhanced phosphatase antibodies.

Also provided by the present invention are purified and isolated Type III density enhanced phosphatase polypeptides, including fragments and variants thereof. A preferred Type III density enhanced phosphatase polypeptide is set forth in SEQ ID NO: 2. Novel Type III density enhanced phosphatase polypeptides and variant polypeptides may be obtained as isolates from natural sources, but are preferably produced by recombinant procedures involving host cells of the invention. Completely glycosylated, partially glycosylated and wholly un-glycosylated forms of the Type III density enhanced phosphatase polypeptide may be generated by varying the host cell selected for recombinant production and/or post-isolation processing. Variant Type III density enhanced phosphatase polypeptides of the invention may comprise water soluble and insoluble polypeptides including analogs wherein one or more of the amino acids are deleted or replaced: (1) without loss, and preferably with enhancement, of one or more biological activities or immunological characteristics specific for Type III density enhanced phosphatases; or (2) with specific disablement of a particular ligand/receptor binding or signalling function.

Also comprehended by the present invention are peptides, polypeptides, and other non-peptide molecules which specifically bind to Type III density enhanced phosphatases of the invention. Preferred binding molecules include antibodies (e.g., monoclonal and polyclonal antibodies, single chain antibodies, chimeric antibodies, anti-idiotype antibodies, CDR-grafted antibodies and the like), counterreceptors (e.g., membrane-associated and soluble forms) and other ligands (e.g., naturally occurring or synthetic molecules), including those which competitively bind Type III density enhanced phosphatases in the presence of anti-Type III density enhanced phosphatase monoclonal antibodies and/or specific counterreceptors. Binding molecules are useful for purification of Type III density enhanced phosphatase polypeptides of the invention and for identifying cell types which express the polypeptide. Binding molecules are also useful for modulating (i.e., inhibiting, blocking or stimulating) the in vivo binding and/or signal transduction activities of Type III density enhanced phosphatases.

Hybridoma cell lines which produce antibodies specific for Type III density enhanced phosphatases are also comprehended by the invention. Techniques for producing hybridomas which secrete monoclonal antibodies are well known in the art. Hybridoma cell lines may be generated after immunizing an animal with a purified Type III density enhanced phosphatase, or variants thereof, or cells which express a Type III density enhanced phosphatase or a variant thereof on the extracellular membrane surface. Immunogen cell types include cells which express a Type III density enhanced phosphatase in vivo, or transfected or transformed prokaryotic or eukaryotic host cells which normally do not express the protein in vivo.

The value of the information contributed through the disclosure of the DNA and amino acid sequences of human DEP-1 is manifest. In one series of examples, the disclosed human DEP-1 cDNA sequence makes possible the isolation of the human DEP-1 genomic DNA sequence, including transcriptional control elements. Transcriptional control elements comprehended by the invention include, for example, promoter elements and enhancer elements, as well as elements which contribute to repression, or downregulation, of mRNA transcription. Control elements of this type may be 5' DNA sequences or 3' DNA sequences with respect to the protein-encoding structural gene sequences, and/or DNA sequences located in introns. The 5' and/or 3' control elements may be proximal and/or distal the protein-encoding sequences of the structural gene. Identification of DNA sequences which modulate mRNA transcription in turn permits the identification of agents which are capable of effecting transcriptional modulation.

In another aspect, identification of polynucleotides encoding other Type III density enhanced phosphatases, huDEP-1 allelic variants and heterologous species (e.g., rat or mouse) DNAs is also comprehended. Isolation of the huDEP-1 genomic DNA and heterologous species DNAs may be accomplished by standard nucleic acid hybridization techniques, under appropriately stringent conditions, using all or part of the DEP-1 DNA or RNA sequence as a probe to screen an appropriate library. Alternatively, polymerase chain reaction (PCR) using oligonucleotide primers that are designed based on the known nucleotide sequence can be used to amplify and identify other cDNA and genomic DNA sequences. Synthetic DNAs encoding Type III density enhanced phosphatase polypeptide, including fragments and other variants thereof, may be synthesized by conventional methods.

DNA sequence information of the invention also makes possible the development, by homologous recombination or "knockout" strategies [see, e.g., Capecchi, *Science* 244:1288–1292 (1989)], of rodents that fail to express a functional Type III density enhanced phosphatase polypeptide or that express a variant Type III density enhanced phosphatase polypeptide. Such rodents are useful as models for studying the activities of Type III density enhanced phosphatases and modulators thereof in vivo.

DNA and amino acid sequences of the invention also make possible the analysis of Type III density enhanced phosphatase regions which actively participate in counterreceptor binding, as well as sequences which may regulate, rather than actively participate in, binding. Identification of motifs which participate in transmembrane signal transduction is also comprehended by the invention. Also comprehended is identification of motifs which determine subcellular localization of the immature and mature Type III density enhanced phosphatase proteins.

DNA of the invention is also useful for the detection of cell types which express Type III density enhanced phosphatase polypeptides: Identification of such cell types may have significant ramifications for development of therapeutic and prophylactic agents. Standard nucleic acid hybridization techniques which utilize e.g., huDEP-1 DNA to detect corresponding RNAs, may be used to determine the constitutive level of Type III density enhanced phosphatase transcription within a cell as well as changes in the level of transcription in response to internal or external agents. Identification of agents which modify transcription, translation, and/or activity of Type III density enhanced phosphatases can, in turn, be assessed for potential therapeutic or prophylactic value. DNA of the invention also makes possible in situ hybridization of e.g., huDEP-1 DNA to cellular RNA, to determine the cellular localization of Type III density enhanced phosphatase specific messages within complex cell populations and tissues.

Polynucleotides of the present invention also provide a method whereby substrate or other molecules which interact with Type III density enhanced phosphatases can be identified. A presently preferred method for identifying interacting molecules comprises the steps of: a) transforming or transfecting appropriate host cells with a DNA construct comprising a reporter gene under the control of a promoter regulated by a transcription factor having a DNA-binding domain and an activating domain; b) an optional step of cotranforming or co-transfecting the same host cells with a protein tyrosine kinase (e.g., v-src, c-src or the like) in order to phosphorylate potential interacting components and/or substrates introduced as in (d) below; c) expressing in the host cells a first hybrid DNA sequence encoding a first fusion of part or all of e.g., a huDEP-1 isoform and either the DNA-binding domain or the activating domain of the transcription factor; d) expressing in the host cells a library of second hybrid DNA sequences encoding second fusions of part or all of putative DEP-1 isoform-binding proteins and either the activating domain or DNA binding domain of the transcription factor which is not incorporated in the first fusion; e) detecting binding of DEP-1 isoform-binding proteins to the DEP-1 isoform in a particular host cell by detecting the production of reporter gene product in the host cell; and f) isolating second hybrid DNA sequences encoding DEP-1 isoform-binding protein from the particular host cell. Variations of the method altering the order in which e.g., the huDEP-1 isoforms and putative huDEP-1 isoform-binding proteins are fused to transcription factor domains, either at the amino terminal or carboxy terminal end of the transcription factor domains, are contemplated. In a preferred method, the promoter is the ADHI promoter, the DNA-binding domain is the lecA DNA-binding domain, the activating domain is the GAL4 transactivation domain, the reporter gene is the lacZ gene and the host cell is a yeast host cell. Those of ordinary skill in the art will readily envision that any of a number of other reporter genes and host cells are easily amenable to this technique. Likewise, any of a number of transcription factors with distinct DNA binding and activating domains can be utilized in this procedure, either with both the DNA binding and activating domains derived from the same transcription factor, or from different, but compatible transcription factors. As another variation of this method, mutant DEP-1 polypeptides, wherein a cysteine residue in the catalytic domain has been substituted with a serine residue, can be employed in this technique. Mutations of this type have been demonstrated with other phosphatases to recognize and bind substrates, but do not dephosphorylate the substrate since the phosphatase is inactive as a result of the mutation.

An alternative identification method contemplated by the invention for detecting proteins which bind to a Type III density enhanced phosphatase isoform comprises the steps of: a) transforming or transfecting appropriate host cells with a hybrid DNA sequence encoding a fusion between a putative Type III density enhanced phosphatase isoform-binding protein and a ligand capable of high affinity binding to a specific counterreceptor; b) expressing the hybrid DNA sequence in the host cells under appropriate conditions; c) immobilizing fusion protein expressed by the host cells by exposing the fusion protein to the specific counterreceptor in immobilized form; d) contacting a Type III density enhanced phosphatase isoform with the immobilized fusion protein; and e) detecting the Type III density enhanced phosphatase isoform bound to the fusion protein using a reagent specific for the Type III density enhanced phosphatase isoform. Presently preferred ligands/counterreceptor combinations for practice of the method are glutathione-S-transferase/glutathione, hemagglutinin/hemagglutinin-specific antibody, polyhistidine/nickel and maltose-binding protein/amylose.

Additional methods to identify proteins which specifically interact with Type III density enhanced phosphatase (i.e., substrates, ligands, modulators, etc.) are also contemplated by the invention. In one example, purified and isolated Type III density enhanced phosphatase polypeptide (e.g., huDEP-1 polypeptide) can be covalently coupled to an immobilized support (i.e., column resins, beads, etc.) and incubated with cell lysates to permit protein/protein interactions. Proteins which interact with the immobilized DEP-1 polypeptide can then be eluted from the support with gradient washing techniques which are standard in the art.

As another example, protein overlay techniques can be employed. DNA from cells which either express e.g., huDEP-1 or express polypeptides which can modulated or bind to huDEP-1, can be isolated and a library constructed by standard methods. This library can then be expressed in a heterologous cell line and resulting colonies transferred to an immobilizing support. Expressed proteins from these colonies are then contacted with DEP-1 and incubated under appropriate conditions to permit DEP-1/protein interactions. The resulting Type III density enhanced phosphatase/protein complexes formed can be detected by incubation with a specific Type III density enhanced phosphatase antibody. Colonies which interact with the specific antibody contain DNA encoding a protein which interacts with the Type III density enhanced phosphatase. Alternatively, cell or tissue lysates may be employed in this technique, using cells or tissues which normally express DEP-1, or cells which have been previously transfected or transformed with DEP-1 encoding DNA.

BRIEF DESCRIPTION OF THE DRAWING

Numerous other aspects and advantages of the present invention will be apparent upon consideration of the following detailed description thereof, reference being made to the drawing wherein.

DETAILED DESCRIPTION OF THE INVENTION

Figure 1:
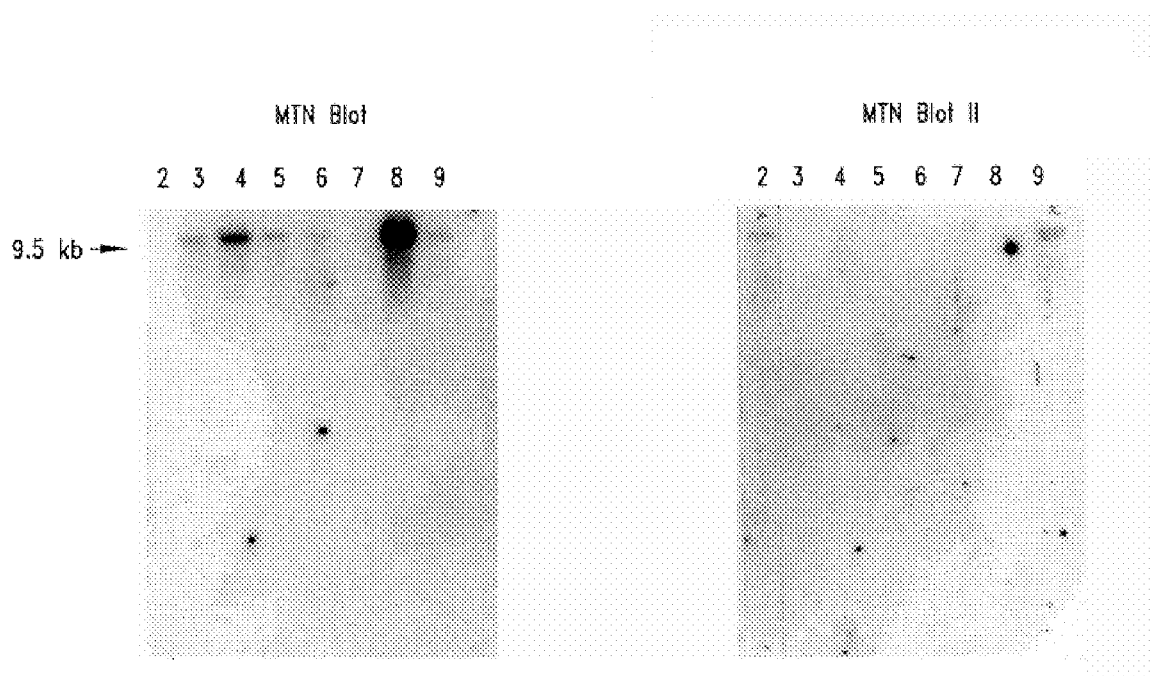
FIGS. 1A through 1B are photographs of Northern blot analysis autoradiograms.

The present invention is illustrated by the following examples relating to the isolation and characterization of genes encoding Type III density enhanced phosphatase polypeptides. Example 1 relates to the isolation of cDNA encoding human DEP-1. Example 2 discusses the tissue distribution of huDEP-1 as determined by Northern blot analysis. Example 3 addresses the generation of antibodies specific for DEP-1 and fragments thereof. Example 4 demonstrates expression of a huDEP-1 cDNA clone in COS cells. Example 5 relates to detection of endogenous expression of huDEP-1 in fibroblast cells. Example 6 addresses expression of huDEP-1 as a function of cell culture density. Example 7 relates to identification of ligands of huDEP-1. Example 8 discusses identification of modulators and substrates of huDEP-1 activity. Example 9 details characterization of the genomic huDEP-1 DNA.

EXAMPLE 1

Isolation and Characterization of huDEP-1 cDNA

In initial efforts to isolate cDNA encoding a novel human phosphatase regulated by a cell density-dependent mechanism, PCR primers were synthesized based on conserved amino acid sequences common to many previously identified phosphatases. These primers were then used to amplify polynucleotides from a cDNA library, the resulting amplification products were sequenced, and these sequences compared to previously reported DNA sequences.

Degenerate primers, corresponding to conserved PTP amino acid sequences set out in SEQ ID NO: 3 and SEQ ID NO: 4, were synthesized and used to prime a PCR with a HeLa cell cDNA library as template.

| KCAQYWP | SEQ ID NO: 3 |
|---|---|
| HCSAGIG | SEQ ID NO: 4 |

The corresponding primers used in the PCR reaction are set forth in SEQ ID NO: 5 and SEQ ID NO: 6, respectively, employing nucleotide symbols according to 37 U.S.C. §1.882.

| 5'-AARTGYGCNCARTAYTGGCC-3' | SEQ ID NO: 5 |
|---|---|
| 3'-GTRACRTCRCGNCCITADCC-5' | SEQ ID NO: 6 |

Sequencing of seventy-seven independent subclones revealed seven distinct sequences, six of which corresponded to PTPs for which DNA sequences had previously been published, and included PTP1B [Tonks, et al., *J.Biol.Chem* 263:6722–6730 (1988)], TCPTP [Cool, et al., *Proc.Natl.Acad.Sci(USA)* 86:5257–521 (1989)], RPTPα [Krueger, et al., *EMBO J*. 9:3241–3252 (1990)], LAR [Streuli, et al., *J.Exp.Med*. 168:1523–1530 (1988)], PTPH1 [Yang and Tonks, *Proc.Natl.Acad.Sci.(USA)* 88:5949–5953 (1991)], and PTPμ [Gebbink, et al., *FEBS Lett.* 290:123–130 (1991)]. The seventh clone was determined to comprise a unique 300 bp PCR fragment and was used to screen an oligo-dT-primed HeLa cell cDNA library (Stratagene, La Jolla, Calif.) in an effort to isolate a corresponding full-length cDNA. Approximately $1.8 \times 10^6$ phage plaques were screened as previously described [Yang and Tonks, *Proc.Natl.Acad.Sci.(USA)* 88:5949–5953 (1991)] and twenty-four positive clones were identified. The largest insert, a 5.1 kb cDNA, was cloned into pUC119, sequenced by the dideoxy chain termination method, and found to contain an open reading frame of 4011 nucleotides encoding a novel receptor-like PTP of 1337 amino acids. The DNA sequence of the 5.1 kb insert is set out in SEQ ID NO: 1, and its predicted amino acid sequence is set out in SEQ ID NO: 2. This human density-enhanced PTP was designated huDEP-1.

The proposed initiating ATG codon of the huDEP-1 gene is flanked by a purine (G) at the −3 position and is thus in agreement with the Kozak rules for initiation [Kozak, *J. Cell Biol*. 108:229–241 (1989)]. There is an in-frame stop codon approximately 290 bp upstream of the predicted initiation site, and the initiating ATG is followed by a hydrophobic region that may serve as a signal sequence. Based on the statistical analysis of known cleavage sites for the signal peptidase [von Heijne, *Nuc.Acids Res.* 14:4683–4690 (1986)], the amino terminus of the mature huDEP-1 polypeptide is assigned to Gly$^{37}$. A second hydrophobic region is found between amino acids 977 and 996, and is followed by a stretch of predominantly basic residues, characteristic of a stop transfer sequence. Therefore, an extracellular region of 940 amino acids and an intracellular portion of 341 amino acids are predicted for the mature huDEP-1 protein. The extracellular domain comprises eight FNIII domains, and thirty-three potential sites for N-linked glycosylation are predicted. Thus, huDEP-1 conforms to the RPTP Type III topography according to the nomenclature of Fischer et al., supra. Unlike most RPTPs which possess a tandem repeat of catalytic domains, the cytoplasmic region contains a single catalytic domain spanning amino acid residues 1060 through 1296. Human DEP-1 is therefore representative of an expanding group of RPTPs with a single catalytic domain that includes PTPβ [Krueger, et al., *EMBO J*. 9:3241–3252 (1990)], DPTP1OD of Drosophila [Tian, et al., *Cell* 76:675–685 (199 1); Yang, et al., *Cell* 67:661–673 (1991)], DPTP4E of Drosophila [Oon, et al., *J.Biol.Chem*. 268:23964–23971 (1993)], and the recently described SAP-1 enzyme [Matozaki, et al., *J.Biol.Chem*. 269:2075–2081 (1994)]. Amino acid sequence comparison of the catalytic domain of huDEP-1 with other PTP domains revealed huDEP-1 is most closely related to PTPβ and SAP-1. The sequence includes several Ser-Pro motifs, as well as potential sites for phosphorylation by casein kinase II.

EXAMPLE 2

Northern Analysis of huDEP-1 Tissue Distribution

Because the expression of PTPs has previously been demonstrated to be ubiquitous in eukaryotes, various human tissues were analyzed in order to determine the relative degree of huDEP-1 mRNA expression.

RNA Multi Tissue Northern blot filters (Clontech, Palo Alto, Calif.), containing immobilized RNA from various human tissues, were probed with a 1.6 kb HindIII/EcoRI fragment of the huDEP-1 cDNA previously radiolabeled to a specific activity of $1.5 \times 10^6$ cpm/ng using a Megaprime DNA labeling kit (Amersham, Arlington Heights, Ill.). This probe represented the entire length of the isolated huDEP-1 cDNA. Hybridization was performed for 16 hours at 65° C. in a hybridization buffer containing 0.5 M $Na_2HPO_4$, 7% SDS, 1 mM EDTA, and labeled probe at a concentration of $10^6$ cpm/ml. Filters were then washed 5 times at 65° C. in 40 mM $Na_2HPO_4$, 1% SDS, and 1 mM EDTA. The membrane was then subjected to autoradiography. The results are presented in FIGS. 1A and 1B, wherein the human tissue source of immobilized RNA is as follows. In FIG. 1A, RNA in lane 2 is from heart, lane 3 from brian, lane 4 from placenta, lane 5 from lung, lane 6 from liver, lane 7 from skeletal muscle, lane 8 from kidney, and lane 9 from pancreas. In FIG. 1B, RNA in lane 2 is from spleen, lane 3 from thymus, lane 4 from prostrate, lane 5 from testis, lane 6 from ovary, lane 7 from small intestines, lane 8 from colon, and lane 9 from peripheral blood leukocyte.

Northern analysis indicated that huDEP-1 is expressed in most tissues analyzed, with particularly high mRNA levels detected in placenta, kidney, spleen and peripheral blood leukocytes.

EXAMPLE 3

Generation of huDEP-1 Polyclonal Antibodies

Two peptides, unique to huDEP-1 and corresponding to amino acid residues 1297 through 1315 and residues 1321 through 1334 in SEQ ID NO: 2 (downstream from the catalytic region) were synthesized with an additional amino terminal cysteine residue and conjugated to rabbit serum albumin (RSA) with m-maleimido benzoic acid N-hydroxysuccinimide ester (MBS)(Pierce, Rockford, Ill.). Immunization protocols with these peptides were performed by Cocalico Biologicals (Reamstown, Pa.). Initially, a prebleed of the rabbits was performed prior to immunization. The first immunization included Freund's complete adjuvant and 500 μg conjugated peptide or 100 μg purified peptide. All subsequent immunizations, performed four weeks after the previous injection, included Freund's incomplete adjuvant with the same amount of protein. Bleeds were conducted seven to ten days after the immunizations.

For affinity purification of the antibodies, huDEP-1 peptide conjugated to RSA with MBS, was coupled to CNBr-activated Sepharose (Pharmacia, Uppsala, Sweden). Antiserum was diluted 10-fold in 10 mM Tris-HCl, pH 7.5, and incubated overnight with the affinity matrix. After washing, bound antibodies were eluted from the resin with 100 mM glycine, pH 2.5.

The antibody generated against conjugated amino acid residues 1297 through 1315 was designated anti-CSH-241, and the antibody raised against the conjugated peptide corresponding to amino acid residues 1321 through 1334 was designated anti-CSH-243.

EXAMPLE 4

Expression of huDEP-1 by Transfected Host Cells

To study the protein product of the huDEP-1 cDNA, the 5.1 kb EcoRI insert was cloned into the expression vector pMT2 [Sambrook, et al., *Molecular Cloning: A Laboratory Manual*, Cold Spring Harbor Laboratory Press (1989) pp 16.17–16.22] and transfected into COS cells grown in DMEM supplemented with 10% FCS. Transfections were performed employing calcium phosphate techniques [Sambrook, et al (1989) pp. 16.32–16.40, supra] and cell lysates were prepared forty-eight hours after transfection from both transfected and untransfected COS cells. Lysates were subjected to analysis by immunoblotting using anti-CSH-243 antibody, and PTP assays of immune complexes as addressed below.

In immunoblotting experiments, preparation of cell lysates and electrophoresis were performed. Protein concentration was determined using BioRad protein assay solutions. After semi-dry electrophoretic transfer to nitrocellulose, the membranes were blocked in 500 mM NaCl, 20 mM Tris, pH 7.5, 0.05% Tween-20 (TTBS) with 5% dry milk. After washing in TTBS and incubation with secondary antibodies (Amersham), enhanced chemiluminescence (ECL) protocols (Amersham) were performed as described by the manufacturer to facilitate detection.

For immune complex PTP assays, 60 μg of cell lysate were immunoprecipitated with 20 μl of anti-CSH-243 antisera or preimmune rabbit serum bound to 25 μl of Protein-A Sepharose (Pharmacia). After overnight incubation at 4° C., the immune complexes were washed three times in washing buffer (1% Triton X-100, 150 mM NaCl, 20 mM Hepes, pH 7.5, 5 μg/ml aprotinin, 5 μg/ml leupeptin, 1 mM benzamidine, and 1 mM DTT) and once in assay buffer (25 mM imidazole, pH 7.2, 0.5 mg/ml BSA, and 1 mM DTT). Protein-A Sepharose immune complexes were then resuspended in 150 μl of assay buffer and assayed for PTP activity as triplicates. Assays were performed for 6 minutes at 30° C. in a total volume of 60 μl using 3 μl M [$^{32}$P-Tyr]-reduced carboxymethylated (RCM) lysozyme as substrate (Flint, et al., *EMBO J.* 12:1937–1946 (1993)].

Affinity-purified anti-CSH-243 antibodies specifically detected a protein of 180 kD molecular weight in lysates from transfected cells. Furthermore, when immune complexes were analyzed for PTP activity, almost 10-fold higher activity was detected in anti-CSH-243 immune complexes from the transfected cells compared to the untransfected cells. This PTP activity was largely absent in immune complexes derived from immunoprecipitations with blocked antiserum or preimmune serum. It was concluded that the huDEP-1 cDNA encodes a 180 kD protein with intrinsic PTP activity.

EXAMPLE 5

Endogenous Expression of huDEP-1

To characterize endogenously expressed huDEP-1, lysates from different cell lines including CEM (ATCC CCL 119), HeLa (ATCC CCL 2), 293 (ATCC CRL 1573), Jurkat (ATCC TIB 152), K562 (ATCC CCL243), HL60 (ATCC CCL 240), WI38 (ATCC CCL 75) and AG 1518 (Coriell Cell Repositories, Camden, N.J.) were analyzed by immunoblotting with antibody anti-CSH-243 as described in Example 4.

WI38 cells, a diploid fetal lung fibroblast-like cell line with finite life span, showed the highest expression. Similar levels of expression were also detected in AG 1518 foreskin fibroblast cells.

To further examine the expression of huDEP-1, lysates from metabolically labeled cells were analyzed by immunoprecipitation and SDS-gel electrophoresis. Confluent cultures of WI38 and AG 1518 cells were metabolically labeled for four hours in methionine-free DMEM supplemented with 1 mg/ml bovine serum albumin (BSA) and 0.15 mCi/ml Translabel (ICN, Costa Mesa, Calif.). Cells were lysed in 0.5% DOC, 0.5% Triton X-100, 150 mM NaCl, 20 mM Hepes, pH 7.5, 5 μg/ml aprotinin, 5 μg/ml leupeptin, 1 mM benzamidine, 1 mM DTT (lysis buffer) and lysates were centrifuged at 15,000×g for 15 minutes. Lysates corresponding to approximately 2×10$^6$ cells were then incubated with 20 μl of anti-CSH-243 or anti-CSH-243. After incubation for four hours at 4° C., 50 μl of a 1:1 Protein-A-Sepharose slurry was added to bind the protein/antibody complexes and incubation continued for 60 minutes. Immune complexes adsorbed to the Protein-A-Sepharose were collected by centrifugation and washed three times in 1% Triton X-100, 150 mM NaCl, 20 mM Hepes, pH 7.5, 5 μg/ml aprotinin, 5 μg/ml leupeptin, 1 mM benzamidine, 1 mM DTT (washing buffer) and once in 20 mM Tris, pH 7.5. Samples were eluted from the resin by incubation at 95° C. for 3 minutes in reducing SDS-sample buffer and analyzed by SDS-gel electrophoresis on 7% gels, followed by fluorography.

In both WI38 and AG 1518 cells, a protein of 180 kD was recognized specifically by the unblocked antisera. Anti-CSH-243 antisera immunoprecipitation with WI38 cell lysate also yielded significantly higher amounts (approximately 10 to 20 fold higher) of activity than precipitations with pre-immune serum or antiserum that had been previously incubated with 200 μg/ml of peptide-conjugate.

It appears that huDEP-1 is a phosphoprotein in vivo because the fact that the anti-CSH-243 antibody was capable of immunoprecipitating a 180 kD [$^{32}$P]-labeled protein from a cell lysate of WI38 cells which had been metabolically labelled with [$^{32}$P]-inorganic phosphate.

EXAMPLE 6

Cell Density-Dependent Expression and Activity of huDEP-1.

Figure 2:
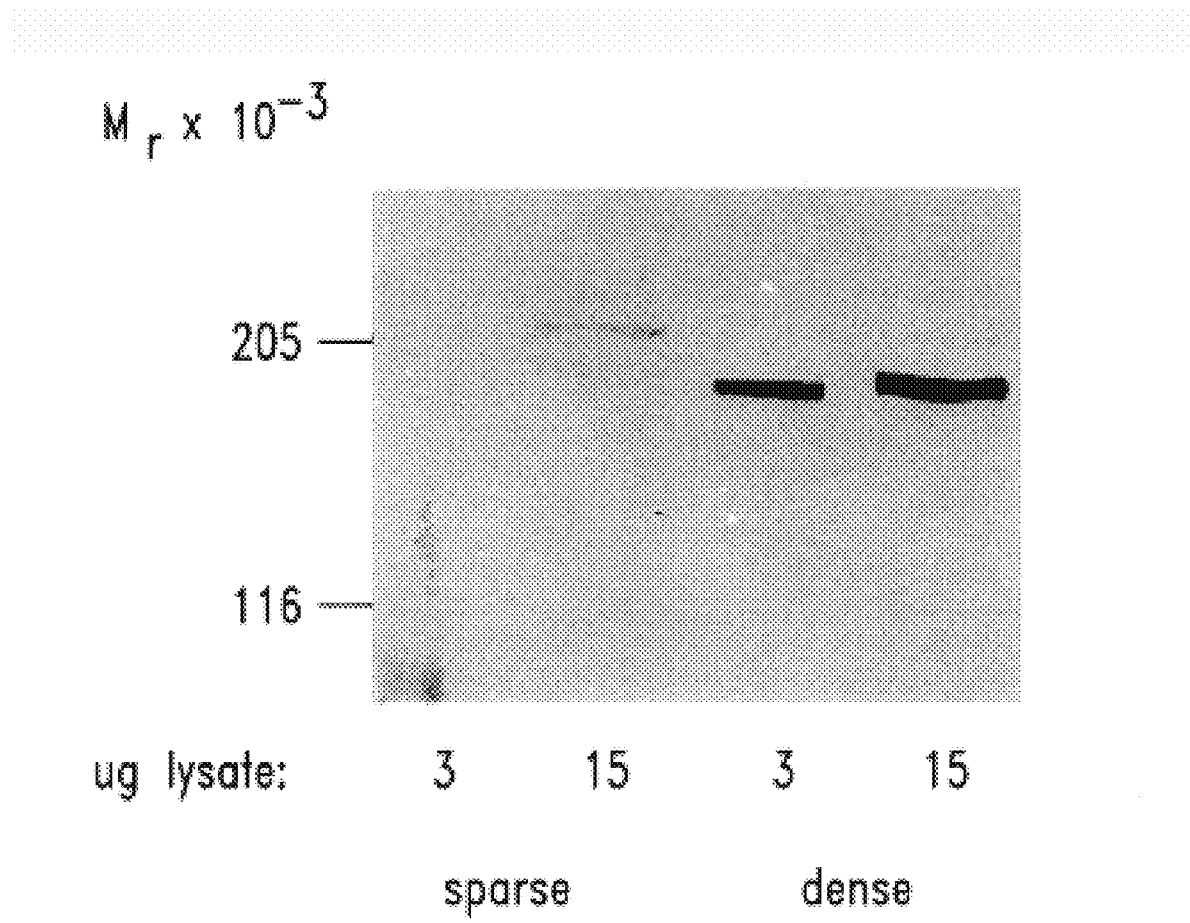
FIG. 2 shows the density-dependent expression of DEP-1.

WI38 cell lysates from sparse (less than 7,000 cells /cm$^2$) or dense (more than 25,000 cells/cm$^2$) cultures were compared for levels of expressed huDEP-1 protein by immunoblotting with anti-CSH-243 antibody as described in Example 4. A dramatic, ten- to twenty-fold increase in huDEP-1 expression was detected in dense cell cultures as shown in FIG. 2. Since 3 µg of total cell lysate from more confluent culture gave a relatively strong signal, and 15 µg of lysates from sparse cultures were below detection, it was estimated that at least 10-fold higher amounts of huDEP-1 are present in cells from dense cultures. Similar results were obtained with anti-CSH-241. When the amounts of PTP1B in cell lysates from sparse and dense cells were compared using an anti-PTP1B monoclonal antibody FG6 (Oncogene Science, Uniondale, N.Y.), no difference was observed. The observed effects on huDEP-1 expression are not restricted to WI38 cells as similar results were obtained in AG 1518 cells.

In order to determine if enzyme activity was also regulated by a density-dependent mechanism, huDEP-1 and PTPIB immune complexes and total cell lysates from both sparse and dense WI38 and AG 1518 cell cultures were also analyzed for phosphatase activity using the PTP assay. For immune complex PTP assays, 60 µg of cell lysate were immunoprecipitated with 20 µl of anti-CSH-243 antisera (with or without pretreatment with antigen) or preimmune serum bound to 25 µl of Protein-A Sepharose. After incubation overnight at 4° C., immune complexes were washed three times in washing buffer and once in 25 mM imidazole, pH 7.2, 0.5 mg/ml BSA, 1 mM DTT (assay buffer). Protein-A-Sepharose immune complexes were then suspended in 150 µl of assay buffer and assayed for PTP activity as triplicates. Assays were performed for 6 minutes at 30° C. in a total volume of 60 µl using 3 µM [$^{32}$P-Tyr] RCM lysozyme as substrate [Flint, et al., supra].

In agreement with the increased huDEP-1 protein expression demonstrated in the immunoblotting experiments, huDEP-1 enzyme activity also increased in the dense cell cultures. The observed increase in activity in huDEP-1/CSH-243 immunoprecipitates from dense cultures (approximately two- to three-fold) was not as great as the observed increase in protein expression in dense cultures, most likely due to incomplete precipitation of all of the PTP using anti-CSH-243 antisera. No difference was observed in activity of PTP1B/FG6 immunoprecipitates or total cell lysates from sparse and dense cell cultures.

Finally, to investigate the kinetics of the density-dependent upregulation of huDEP-1 expression, lysates of WI38 and AG 1518 cells at intermediate cell densities were included in the immunoblotting analysis. The highest expression was found in cells at saturation density, however, at intermediate densities an increase in expression with respect to sparse cell cultures was also observed. Thus, the upregulation of huDEP-1 expression appears to be initiated prior to saturation density and not a result of growth arrest.

While the precise mechanism by which huDEP-1 expression is induced remains unclear, the demonstration that expression was induced in two distinct cell lines as cells approach confluence suggests involvement of huDEP-1 in promoting net dephosphorylation of proteins, countering the effects of growth promoting PTK activity. This possibility, in combination with the broad distribution of huDEP-1 expression, suggests that huDEP-1 may be involved in a general mechanism for contact inhibition of cell growth.

EXAMPLE 7

Identification of DEP-1 Ligands

The possibility that DEP-1 functions as an adhesion molecule will be tested using the Sf9 cell system [Brady-Kalnay, et al., *J. Cell Biol.* 122:961–972 (1993)] following transfection with DEP-1 cDNA. In addition to studies following transient expression, stable cell lines overexpressing DEP-1 will be generated.

If DEP-1 functions as an adhesion molecule, the extracellular counterreceptor(s) will be identified. One possibility is that, like PTPµ, DEP-1 binding is homophilic, where one DEP-1 molecule binds another DEP-1 molecule on an adjacent cell. Alternatively, DEP-1 specifically recognize a non-DEP-1 molecule in a heterophilic binding mechanism.

In addition, a number of deletion and site-directed mutagenesis strategies well known in the art will be applied to identify the important segments in the protein that confer binding specificity. Analysis of 2D gels of proteins that react with anti-phosphotyrosine antibodies, for example monoclonal antibody 4G10 (UBI, Lake Placid, N.Y.), will be used to initiate studies as to the effect on activity of engagement of the extracellular segment of the PTP in either homophilic binding interactions or antibody binding.

Use of "epitope" library technology [Scott and Smith, *Science* 249:386–390 (1990)] will be employed to identify peptide sequences that interact with DEP-1. This approach will prove particularly useful in the search for ligands for DEP-1 whose extracellular segment, comprising multiple FNIII repeats, may bind low $M_r$ factors.

Protein:protein interactions have previously been reported for FNIII sequences and specific binding proteins, and this information will be utilized in several approaches to identify proteins which specifically interact with the extracellular domain of DEP-1. Specifically, protein:protein interactions will be investigated in cell "panning" experiments [Seed and Aruffo, *Proc.Natl.Acad.Sci.(USA)* 84:3365–3369 (1987)], gel overlay assays [Hirsch, et al., *J.Biol.Chem.* 267:2131–2134 (1992); Carr and Scott, *Trends in Biochemical Sci.* 17:246–249 (1992)], band shift analysis [Carr, et al., *J.Biol.Chem.* 267:13376–13382 (1992)], affinity chromatography, screening of expression libraries [Young and Davis, *Proc.Natl.Acad.Sci.(USA)* 80:1194–1198 (1983)], etc.

EXAMPLE 8

Identification of Modulators/Substrates of DEP-1

Potential substrates of predicted physiological relevance will be tested for activity against the catalytic domain in vitro.

In addition, yeast screening systems [Fields and Song, *Nature* 340:245–246 (1989); Yang, et al., *Science* 257:6810682 (1992); Vojtek, et al., *Cell* 74:205–214 (1993)] will be utilized, particularly with reference to co-expression with a protein tyrosine kinase, for example, v-src or c-src, to isolate proteins with the capacity to regulate DEP-1 activity.

In a further attempt to identify substrates for DEP-1, a mutant form in which the cysteinyl residues of the active center has been replaced by serine will be expressed. Recent studies suggest that substrates bind to and remain complexed with the inactive phosphatase. The mutant PTP is capable of binding substrate molecules but traps them in a "dead end" complex that can be isolated by standard immunoprecipitation techniques [Sun, et al., *Cell* 75:487–493 (1993)]. Potential substrates may be co-immunoprecipitated with the mutant PTP from $^{35}$S-labeled cells. Alternatively, wild-type, or native, DEP-1 enzyme may be utilized in this technique. Initial studies in this direction may make use of chimeric molecules, for which antibodies to the extracellular growth factor binding segment are commercially available, while antibodies are raised to the bona fide DEP-1 sequences.

EXAMPLE 9

Characterization of the Genomic DEP-1 Gene

Isolation of the cDNA sequences for DEP-1 will permit the isolation and purification of the corresponding genomic sequences for DEP-1. In preliminary work, it has been demonstrated that huDEP-1 mapped to human chromosome 11p, band 11.2 or the interface of 11.2 and 11.3. Isolation of these genomic DEP-1 sequences will permit the identification of putative regulatory sequences for DEP-1 transcription, and presumably identification of transacting transcriptional modulators of DEP-1 expression. In addition, isolation and purification of the human genomic clone will permit screening of libraries in other species to determine if homologous counterparts exist in the species. Identification of a homologous counterpart in mice will be of particular importance because of the possibility of generating a knock-out strain. Mouse strains which do not express a particular protein are of considerable importance in that they permit determination of indications associated with absence of the protein in a living animal.

While the present invention has been described in terms of specific methods and compositions, it is understood that variations and modifications will occur to those skilled in the art. Therefore, only such limitations as appear in the claims should be placed on the invention.

What is claimed is:

1. An isolated human Type III density enhanced protein-1 tyrosine phosphatase polypeptide (huDEP-1) comprising an amino acid sequence set forth in SEQ ID NO:2.

2. An isolated polypeptide, said polypeptide being immunologically reactive with an antibody that specifically binds to a human Type III density enhanced protein-1 tyrosine phosphatase polypeptide (huDEP-1) polypeptide comprising an amino acid sequence set forth in SEQ ID NO:2.

* * * * *